US006558323B2

(12) United States Patent
Wakabayashi et al.

(10) Patent No.: US 6,558,323 B2
(45) Date of Patent: May 6, 2003

(54) ULTRASOUND TRANSDUCER ARRAY

(75) Inventors: Katsuhiro Wakabayashi, Hachioji (JP); Yukihiko Sawada, Tokorozawa (JP); Sayuri Sato, Hino (JP); Akiko Mizunuma, Hachioji (JP); Takuya Imahashi, Kawasaki (JP); Tomoki Funakubo, Hachioji (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/998,982

(22) Filed: Nov. 30, 2001

(65) Prior Publication Data

US 2002/0156373 A1 Oct. 24, 2002

(30) Foreign Application Priority Data

Nov. 29, 2000 (JP) ....................................... 2000-363641
Jan. 30, 2001 (JP) ....................................... 2001-022202
Feb. 20, 2001 (JP) ....................................... 2001-043785

(51) Int. Cl.[7] .................................................. A61B 8/00
(52) U.S. Cl. ....................................... 600/437; 600/457
(58) Field of Search ................................ 600/437, 443, 600/459, 462, 463; 73/642; 204/197

(56) References Cited

FOREIGN PATENT DOCUMENTS

JP 56091201 7/1981
JP 61253999 11/1986
JP 622813 1/1987
JP 161062 12/1989
JP 09139998 5/1997

OTHER PUBLICATIONS

English translation of Abstract of Japanese Patent No. 61–253999 dated Nov. 11, 1986.
English translation of Abstract of Japanese Patent No. 09–139998 dated May 27, 1997.
English translation of Japanese Gazette Scope of Claim for Patent No. Hei 1–61062 dated Dec. 27, 1989.
English translation of Abstract of Japanese Patent No. 56–091201 dated Jul. 24, 1981.
English translation of Japanese Gazette Scope of Claim for Patent No. Shō 62–2813 dated Jan. 21, 1987.

*Primary Examiner*—Francis J. Jaworski
*Assistant Examiner*—Maulin Patel
(74) *Attorney, Agent, or Firm*—Ostrolenk, Faber, Gerb & Soffen, LLP

(57) ABSTRACT

By bonding a conductive first matching layer 14 to the acoustic radiation surface side, which is the bottom side, of a belt-shape piezoelectric element on both faces with electrodes provided, and using a dicing machine to form divided grooves 16, an array of piezoelectric elements 6, 6, . . . , 6 is formed in the element array direction. By deepening the divided grooves 16, generation of cross talk can be prevented, and by filling the portions of the divided grooves 16 not in contact with the piezoelectric elements 6 with a conductive adhesive 17, a reduction in strength due to formation of the divided grooves 16 can be prevented, and a common connection between the ground electrode 13*b* on the bottom surface of each piezoelectric element 6 and the conductive first matching layer 14 can be reliably secured.

22 Claims, 18 Drawing Sheets w/t=0.8

ULTRASOUND TRANSDUCER ARRAY

This application claims benefit of Japanese Application Nos. 2001-22202, filed in Japan on Jan. 30, 2001; 2001-43785, filed in Japan on Feb. 20, 2001; and 2000-363641, filed in Japan on Nov. 29, 2000, the contents of which are incorporated by this reference.

BACKGROUND OF THE INVENTION

1. Field of the Invention

This invention relates to an ultrasound transducer array, used in ultrasound diagnosis for medical use or for non-destructive inspection.

2. Description of the Related Art

In recent years, ultrasound diagnostic equipment using ultrasound transducers has come into widespread use in medical diagnostics and other fields. In addition to mechanical scanning-type ultrasound transducers which rotate a single ultrasound transducer or similar to mechanically scan with ultrasound, electronic scanning-type ultrasound transducers have also been adopted.

Such electronic scanning-type ultrasound transducers are formed using ultrasound transducer arrays, in which ultrasound transducers are formed in an array shape.

Conventional electronic scanning-type ultrasound transducers (ultrasound transducer arrays) provide signal electrodes and ground electrodes on each side of a piezoelectric element, and one or more grooves, extending to a depth partway through a provided matching layer, to divide the element and form a plurality of elements. Here, the ground electrodes must be connected to a common line.

As a method of connecting the ground electrodes to a common line, the matching layer adjacent to the piezoelectric element may be made of a conductive resin, and grooves are provided being extended to a depth midway through the matching layer, as in Japanese Unexamined Patent Application Publication No.61-253999.

However, if the thickness of the remaining matching layer is small, the strength of the matching layer is relatively weakened, so that when a force is applied, cracks may appear in the matching layer, or conduction faults may occur.

On the other hand, if the thickness of the remaining matching layer is large (if the groove cut into the matching layer is shallow), cross talk may occur, and the image quality may worsen.

SUMMARY OF THE INVENTION

An object of this invention is to provide a progressive ultrasound transducer array, which prevents the occurrence of cross talk and in which a common connection of the ground electrodes of piezoelectric elements can be reliably secured.

In this invention, an ultrasound transducer array, in which are arranged a plurality of piezoelectric elements, which can be electrically operated independently, comprises one or a plurality of matching layers, provided on the acoustic radiating surface side of the above piezoelectric elements; a conductive material layer, provided on the side of the above matching layers joined with the above piezoelectric elements, in the direction along the array direction, part of which is in contact with and electrically connected to the above piezoelectric elements along the above array direction, and part of which is not in contact with the above piezoelectric elements along the above array direction; a plurality of grooves, which mechanically and electrically insulate at least part of the above piezoelectric elements and the above matching layer for each element which can be electrically operated independently; and, conductive material which fills at least a part of the portions of the above grooves which are formed where the above piezoelectric elements and the above conductive material layer are not in contact.

The above and other objects, features and advantages of the invention will become more clearly understood from the following description, referring to the accompanying drawings.

BRIEF DESCRIPTION OF THE DRAWINGS

FIG. 1 is a perspective view showing the entirety of an ultrasound transducer array;

FIG. 2 is a cross-sectional view showing the cross-sectional structure in the array direction;

FIG. 3 is a cross-sectional view showing the internal structure in the elevation direction;

FIG. 4 is an explanatory diagram showing the internal structure before filling with backing material in FIG. 3;

FIG. 11 is a perspective view showing the appearance of an ultrasound transducer array;

FIG. 12 is a cross-sectional view showing the structure of the element array;

FIG. 13 is a cross-sectional view showing the structure in the elevation direction;

FIG. 14 is a side view of an ultrasound transducer array;

FIG. 15 is a cross-sectional view along line C1—C1 in FIG. 14;

FIG. 16 is a cross sectional view of the layered member of an ultrasound transducer array manufactured using a first manufacturing method;

FIG. 17 is a perspective view of the parent layered member of an ultrasound transducer array manufactured using a second manufacturing method;

FIG. 23 relates to a thirteenth aspect of the invention;

FIG. 24 through FIG. 27 relate to a fourteenth aspect of the invention;

FIG. 25 are first graphs showing the impedance curve with the ratio w/t of the thickness t to the width w of a piezoelectric element varied;

FIG. 26 are second graphs showing the impedance curve with the ratio w/t of the thickness t to the width w of a piezoelectric element varied;

FIG. 27 are third graphs showing the echo waveform and spectrum of an ultrasound transducer array with the ratio w/t of the thickness t to the width w of a piezoelectric element varied;

FIG. 30 are configuration diagrams showing a conventional ultrasound transducer array;

DESCRIPTION OF THE PREFERRED EMBODIMENTS

Figure 1:
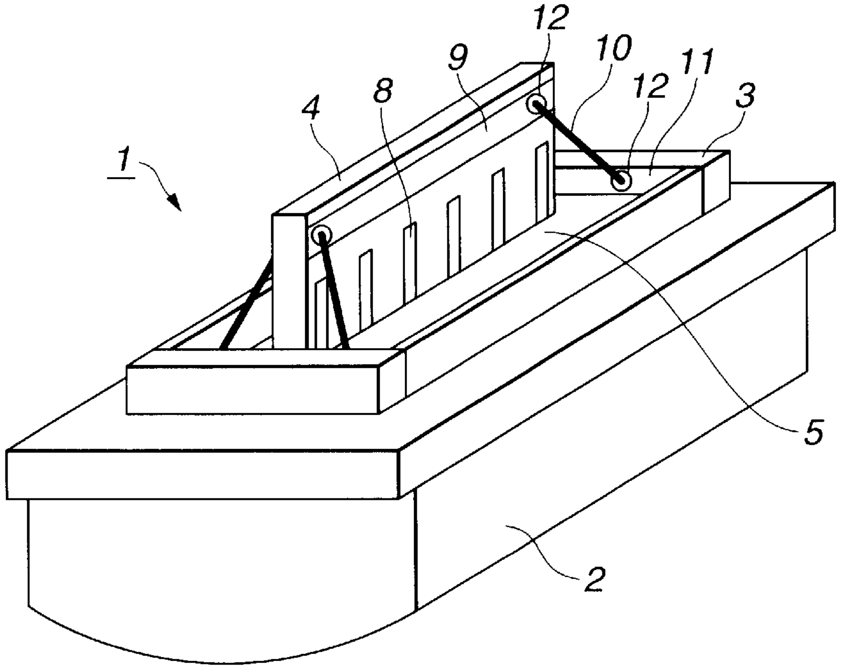
FIG. 1 through FIG. 4 relate to a first aspect of the invention.

Below, first through sixth aspects of this invention are explained, based on FIG. 1 through FIG. 13.

FIG. 1 through FIG. 4 show a first aspect of the invention. The ultrasound transducer array 1 shown in FIG. 1 has a backing material framework 3 positioned on the inside of the acoustic lens 2; a cable wiring board 4 is provided vertically on the inside of this backing material framework 3, and the vicinity of the cable wiring board 4 is filled with backing material 5.

Figure 2:
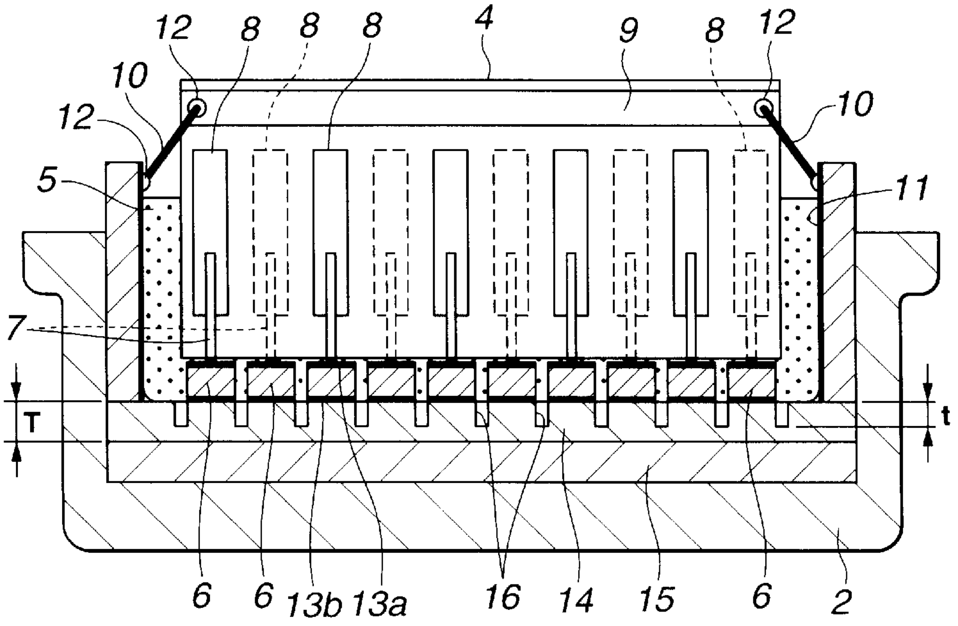

Signal wiring lands 8, 8, . . . , 8, connected by a signal wires 7 to numerous piezoelectric elements 6, 6, . . . , 6 formed in an array shape as shown in FIG. 2, are provided in the length direction on both sides of the cable wiring board 4.

On both surfaces of the cable wiring board 4, near the top, GND wiring lands 9 are formed in a strip shape in the length direction, and are electrically connected, for example, by a connection wire 10 at both end positions by a conducting film 11 provided on the inner face of the backing material framework 3 and by solder 12 or similar.

Figure 3:
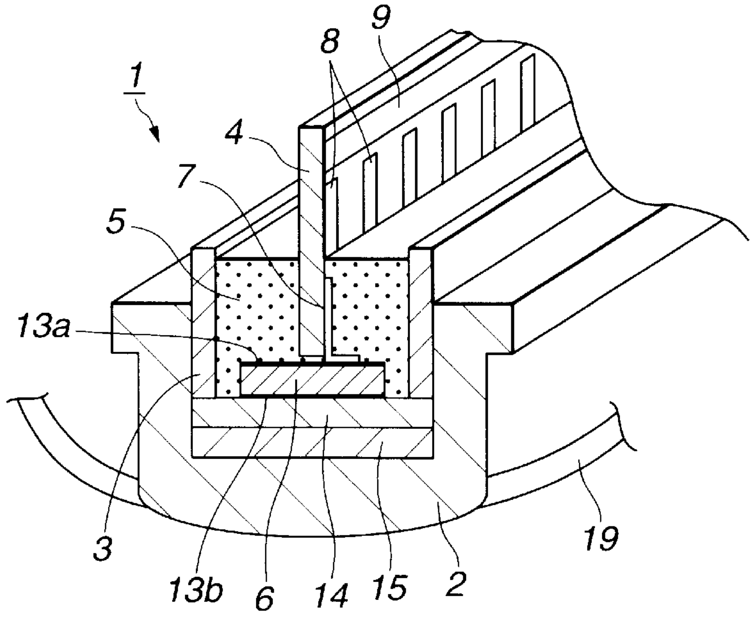
Figure 4:
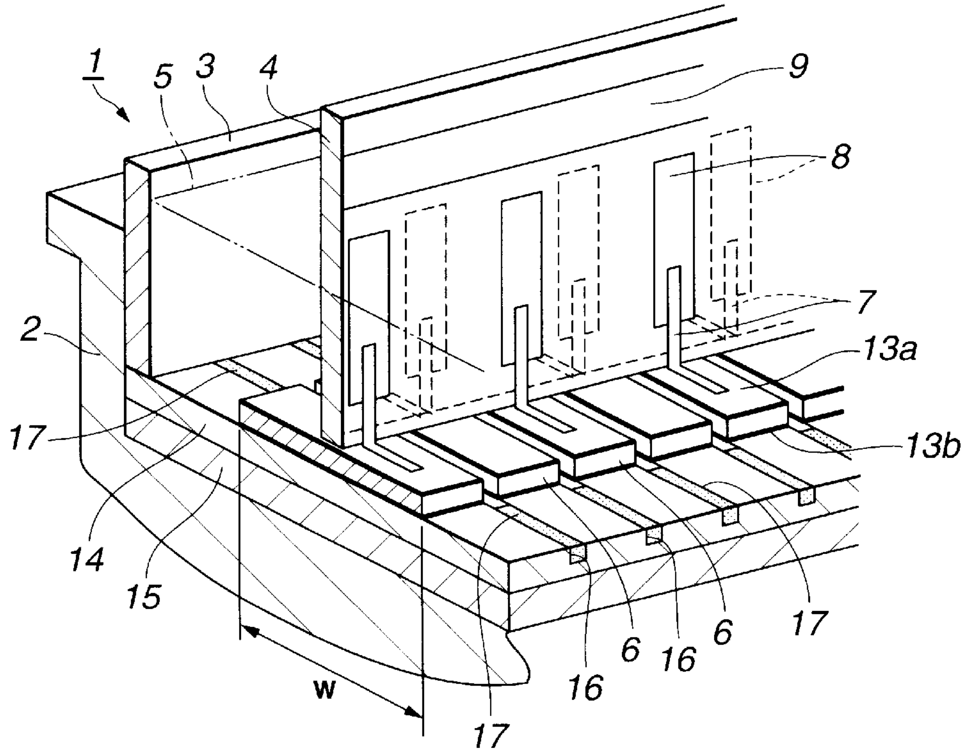

As shown in FIG. 2, FIG. 3 and FIG. 4, signal electrodes 13*a* and ground electrodes 13*b* are formed on the upper and lower surfaces of each piezoelectric element 6 by evaporation deposition of gold, silver or some other metal, or by some other means; on the lower side (the acoustic radiation side), at which transmission and reception of ultrasound waves is performed, a first matching layer 14 and second matching layer 15 for matching, and an acoustic lens 2 to concentrate the emitted ultrasound waves, are formed in layers.

In this aspect, the first matching layer 14 is formed from a conductive resin (for example, an epoxy resin with carbon or a carbon composite material added) or similar. That is, the first matching layer 14 is conducted to a line common with each electrode 13 serving as the ground electrode on the lower side of each piezoelectric element 6, provided on the side of the first matching layer 14.

The numerous piezoelectric elements formed in an array shape (as an array-shape transducer) 6, 6, . . . , 6 have, for example, a width in the elevation direction (width direction) of w, as shown in FIG. 4. A belt-shaped piezoelectric element board is cut to form divided grooves 16 at a prescribed pitch in the element array direction, and long in the element array direction perpendicular to the width direction. At this time, the dicing machine on both cuts the piezoelectric element board, adhered to the first matching layer 14, on which full-coverage electrodes on both faces are provided by evaporation deposition.

In this case, the depth of the divided grooves 16 is greater than the thickness of the piezoelectric elements 6, and the grooves are formed so as to penetrate partway in the thickness direction of the first matching layer 14 connected to the ground electrodes 13*b* on the lower faces of the piezoelectric elements 6. More specifically, if as in FIG. 2 the thickness of the first matching layer 14 is T, then divided grooves 16 are formed at a thickness t (thickness t is measured from the lower face of the piezoelectric elements 6) equal to approximately 60 to 100% of the thickness T of the first matching layer 14.

In this way, divided grooves 16 are formed to a depth sufficient to reach the first matching layer 14, and to extend to approximately ⅔ or more of the thickness T of this layer 14; hence the occurrence of cross talk between neighboring piezoelectric elements 6, 6, . . . , 6 can be adequately suppressed by the dividing groove 16 between them.

By increasing the depth of the divided grooves 16, the strength of the first matching layer 14 is relatively decreased (compared with the case in which the depth of the divided grooves 16 is small); but in this aspect, the divided grooves 16 are filled with a conductive adhesive 17 as a filler material (reinforcing material), to prevent a relative decrease in strength of the first matching layer 14.

In this aspect, as this conductive adhesive 17, the same conductive member as the member used to form the first matching layer 14 is impregnated and reinforced. Even if cracks appear in the first matching layer 14, the occurrence of conduction faults can be reliably prevented by this conductive adhesive 17.

This conductive adhesive 17 fills the portion of the divided grooves 16 in the first matching layer 14 other than the portion in contact with the piezoelectric elements 6, as shown in FIG. 4. The ground electrode 13*b* of each piezoelectric element 6 is electrically connected with the first matching layer 14, and as shown in FIG. 2, the first matching layer 14 is electrically connected, by a conducting material (solder), with the conductive film 11 provided on the inner face of the backing material framework 3 near both ends in the array direction.

The backing material framework 3 is formed from, for example, glass-epoxy resin, with copper foil applied to the inner surface to form a conductive film 11. The conductive film 11 is electrically connected at the upper edge to the GND wiring land 9 by a connecting wire 10.

Each signal electrode 13*a* on the upper-face side of each piezoelectric element 6 is electrically connected (by solder or similar) using a signal wire 7 to a signal wiring lands 8 formed in a short strip shape opposite the upper side of each signal electrode 13*a* on the cable wiring board 4, provided vertically such that the lower edge is not in contact with the upper face of each piezoelectric element 6.

In this case, as shown in FIG. 2 and FIG. 4, signal wiring lands 8 are formed, in alternation on both faces of the cable wiring board 4, along the length direction at the same intervals as the array of piezoelectric elements 6. That is, the array pitch on one face is double the array pitch for the piezoelectric elements 6, and on each face, each signal electrode 13*a* is connected to a signal wiring land 8 by a signal wire 7 at every other piezoelectric element 6. In this way, signal wiring lands 8 are provided on each face, and by using a signal wire 7 to connect each signal electrode 13*a* to a signal wiring land 8 at every other piezoelectric element 6, signal electrodes can easily be connected to signal wiring lands 8 even when the array-shape piezoelectric elements 6 are formed with a small pitch.

After connecting each signal electrode 13*a* to a signal wiring land 8 by a signal wire 7, the vicinity of the piezoelectric elements 6 is covered by backing material 5 which absorbs or attenuates ultrasound, as shown in FIG. 3.

Each of the signal wiring lands 8 and the GND wiring land 9 of the cable wiring board 4 are connected, by solder or other means, to one end of an ultrasound cable (not shown). The connector at the other end of the ultrasound cable is connected to ultrasound system.

As shown in FIG. 3, the ultrasound transducer array 1 is mounted such that the portion of the acoustic lens 2 is exposed in an opening provided in a case 19.

An ultrasound transducer array 1 configured in this way may be manufactured as follows.

An unhardened resin in liquid form which forms a second matching layer 15, is poured into a frame member, not shown, and hardened, and the surface is machined to form the second matching layer 15 of prescribed thickness; on top of this the first matching layer 14 is similarly formed, and on top of this, the piezoelectric element board, provided with electrodes on both faces, is bonded. After formation of the second matching layer 15, the frame member is removed.

The piezoelectric element board (.and first matching layer 14) is divided at a prescribed pitch in the length direction using a dicing machine, such that the elements of the piezoelectric element board are completely separated, and divided grooves 16 are formed extending to a depth T which is approximately 60 to 100% of the thickness T of the first matching layer 14 beneath, to form separated array-shape piezoelectric elements 6, 6, . . . , 6.

Next, each dividing groove 16, except for portions neighboring each piezoelectric element 6, is filled with a conductive material, for example the same material as the conductive adhesive 17 used to form the first matching layer 14, and this material is hardened to reinforce the first matching layer 14.

Next, the cable wiring board 4, having signal wiring lands 8 and GND wiring lands 9 on its both faces, is positioned using a jig upward the signal electrodes 13*a* on the upper faces of the piezoelectric elements 6, at for example the center of the effective width w in the elevation direction. Each of the signal electrodes 13*a* on the upper face of the piezoelectric elements 6, 6, . . . , 6 is connected to respective signal wiring lands 8 with signal wires 7.

A rectangular-shape backing material framework 3, with the top and bottom sides open, is mounted so as to surround the array-shape piezoelectric elements 6, 6, . . . , 6 and cable wiring board 4. Copper foil or other conductive film 11 is formed on the inner walls of this backing material framework 3, and as shown in FIG. 2, the bottom-side opening is fixed in place and connected for electrical connection with the first matching layer 14 by means of conductive adhesive. This backing material framework 3 is smaller in size than the inner dimensions of the above frame member.

Thereafter, unhardened backing material 5 is poured up to a prescribed height from the top-side aperture of the backing material framework 3, and hardened. Then, the jig which had held the cable wiring board in place is removed, and the conductive film 11 of the backing material framework 3 is electrically connected to the GND wiring lands 9 of the cable wiring board using connecting wire 10. An assembly fabricated in this way is housed in an acoustic lens 2 (not shown) formed in advance using a frame member, and joined such that the second matching layer 15 on the bottom is in contact with the top surface of the acoustic lens 2.

An ultrasound cable, not shown, is connected to the cable wiring board 4, and the connection portion is covered. The ultrasound transducer array 1 manufactured in this manner is mounted in the case 19 such that the bottom side of the acoustic lens 2 is exposed, as shown in FIG. 3.

The operation of an ultrasound transducer array 1 manufactured in this manner is next explained.

The connector at the other end of the ultrasound cable is connected to ultrasound system, the power to the ultrasound system is turned on, and on applying the bottom face of the acoustic lens 2 to the site for inspection of the patient or similar, transmission pulses which perform electric scanning are applied to this ultrasound transducer array 1.

Transmission pulses are applied in order across the signal electrodes 13*a* and ground electrodes 13*b* for each piezoelectric element in the element array direction of the ultrasound transducer array 1, and as a result of application of these transmission pulses, the electro-acoustic transduction function of the piezoelectric elements 6 causes ultrasound excitation, so that ultrasound is emitted toward the bottom face (acoustic radiation face) and the top face. On the top-face side, the ultrasound is attenuated by the backing material 5. On the other hand, the ultrasound emitted from the bottom-face side passes through the first matching layer 14 and second matching layer 15, is focused by the acoustic lens 2, and is sent toward the site for inspection in contact with this acoustic lens 2; at this time, linear scanning is performed in the element array direction.

Reflected ultrasound, reflected by the portion of the inspection site at which the acoustic impedance changes, is received by the same piezoelectric elements 6, converted into electrical signals, subjected to signal processing by the signal processing system within the ultrasound system, and converted into image signals, and an ultrasound cross-sectional image is displayed on a monitor display screen for the case of linear scanning.

When a transmission pulse is applied across the signal electrode 13*a* and ground electrode 13*b* of a piezoelectric element 6, the transmission pulse is applied over a route as follows: signal wiring land 8 of cable wiring board 4 → signal wire 7 → signal electrode 13*a* of piezoelectric element 6 → ground electrode 13*b* → first matching layer (conductive adhesive 17 in dividing groove 16) → conductive film 11 on inner face of backing material framework 3 → connecting wire 10 → ground wiring land 9 of cable wiring board 4.

By means of this ultrasound transducer array 1, by forming deep divided grooves 16 extending to, for example, approximately ⅔ the thickness T of the first matching layer 14, cross talk between neighboring piezoelectric elements 6 in particular can be kept small. Hence cross-sectional images with high resolution in the element array direction can be obtained.

By forming deep divided grooves 16, the strength is reduced compared with the case of shallow grooves; but by filling the divided grooves 16 with a reinforcing conductive adhesive 17, this reduction in strength can be prevented.

When deep divided grooves 16 are formed, even if cracks appear in the first matching layer 14 formed from conductive material, the strength is reinforced as a result of filling the divided grooves 16 with the conductive adhesive 17, and in addition conductive properties are more reliably secured, so that the connection of the ground electrodes 13*b* to a common line can be maintained adequately.

The advantageous results of this aspect are as follows.

By forming deep divided grooves 16, extending to for example approximately 60 to 100% of the thickness T of the first matching layer 14, cross talk can be reduced sufficiently. And, by filling the divided grooves 16 with a conductive adhesive 17, a reduction in strength can be prevented. Also, a common connection of the ground electrodes 13*b* of the piezoelectric elements 6 can be reliably secured.

Figure 5:
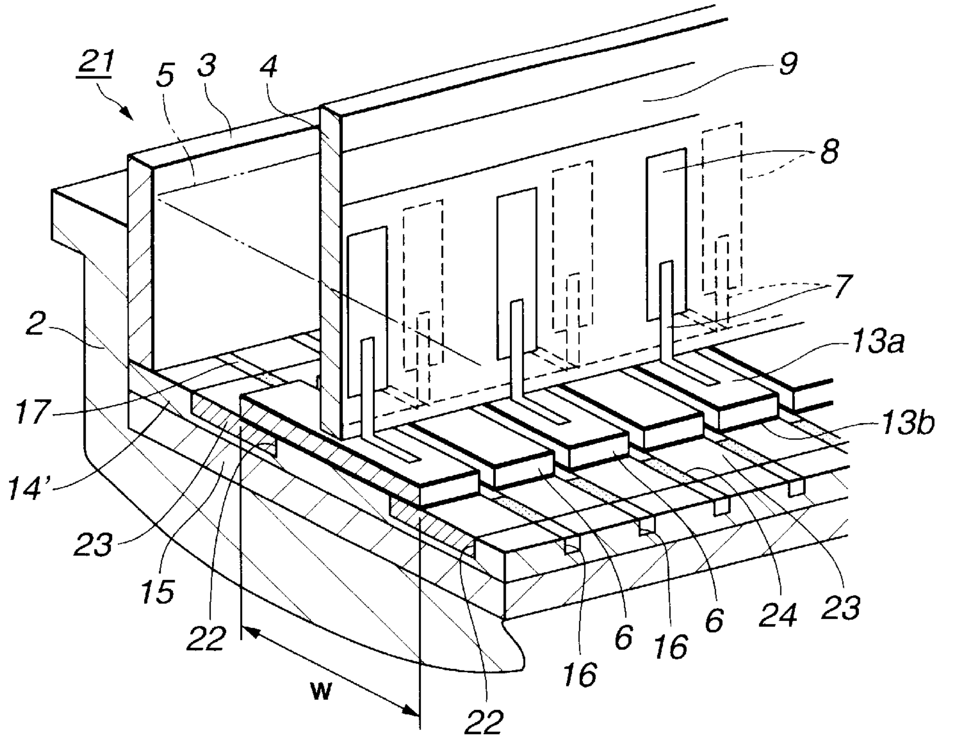
FIG. 5 is an explanatory diagram showing the internal structure of the ultrasound transducer array of a second aspect of the invention.

Next, the structure of an ultrasound transducer array of a second aspect of this invention is explained, referring to FIG. 5.

In this ultrasound transducer array 21, the first matching layer 14 made from conductive material in the ultrasound transducer array shown in FIG. 4 is replaced by a first matching layer 14' not having conductivity; groove portions 22, 22 are formed in this first matching layer 14' along the element array direction in two places where both ends of piezoelectric elements 6 make contact in the elevation direction, and conductive layers 23 are provided in each of these groove portions 22.

Because the conductor which forms the conductive layer 23 is fabricated by mixing a resin and metal powder or similar, it tends to swell on contact with water or other substances. Hence in this aspect, the conductive layer 23 is made 60 to 100% of the thickness of the first matching layer, and at least the second matching layer is reserved, in order to ensure the necessary durability.

In this aspect, when forming the divided grooves 16, the divided grooves 16 are formed more shallow than the thickness of the conductive layer 23, so that formation of the divided grooves 16 does not cause the conductive layer 23 to be separated.

Polishing or other machining is performed in order that the upper face of the first matching layer 14' and the upper face of the conductive layer 23 are in a single plane, and by bonding the piezoelectric element board with electrodes provided on both faces onto the first matching layer 14 and onto the conductive layer 23 formed in the groove portions 22, and using a dicing machine to form the divided grooves 16 similarly to the first aspect, a piezoelectric element array 6, 6, . . . , 6 is formed in which signal electrodes 13*a* and ground electrodes 13*b* are formed on the upper and lower faces respectively.

Here, the upper surface of the first matching layer 14' makes contact with the central portion of the ground electrodes 13*b* on the bottom face of each piezoelectric element 6, and the ground electrodes 13*b* on both ends in the elevation direction make contact with the conductive layer 23.

In this aspect, the portion of the divided grooves 16 which, for example, is not in contact with the piezoelectric elements 6, but which is formed in the conductive layer 23, is filled with a conductive adhesive 24 as a filler material.

As the conductive layer 23 and conductive adhesive 24, an epoxy resin with additive like carbon or a carbon composite material or similar may be adopted, for example, to impart electrical conductivity, as the case in forming the first matching layer 14 explained in the first aspect.

Further, a thermosetting resin may be adopted as the conductive layer 23 and conductive adhesive 24. In this case, the same thermosetting resin material may be adopted in both the conductive layer 23 and conductive adhesive 24. These thermosetting resins include resins which harden at room temperature.

The configuration is otherwise similar to that of the first aspect.

As one effect of this aspect, the central portion of each piezoelectric element 6 makes contact with the first matching layer 14', and both ends make contact only with the conductive layer 23, so that there are fewer constraints on the conductive material properties of the material of the first matching layer 14' compared with the first matching layer 14; hence matching is possible at more appropriate values, and more inexpensive material can be used in manufacture.

In this aspect, part of the ultrasound transmitted from the acoustic radiation surface side of the piezoelectric elements 6 which is formed by the first matching layer 14' is mainly used in formation of ultrasound images.

Other effects are similar to those of the first aspect.

The advantageous results of this aspect are as follows.

Compared with the constraint of conductive properties imposed on the first matching layer 14, there are fewer material constraints, so that matching can be performed at more appropriate values, and more inexpensive materials can be used in manufacturing. Otherwise, the advantageous results are substantially the same as for the first aspect.

Figure 6:
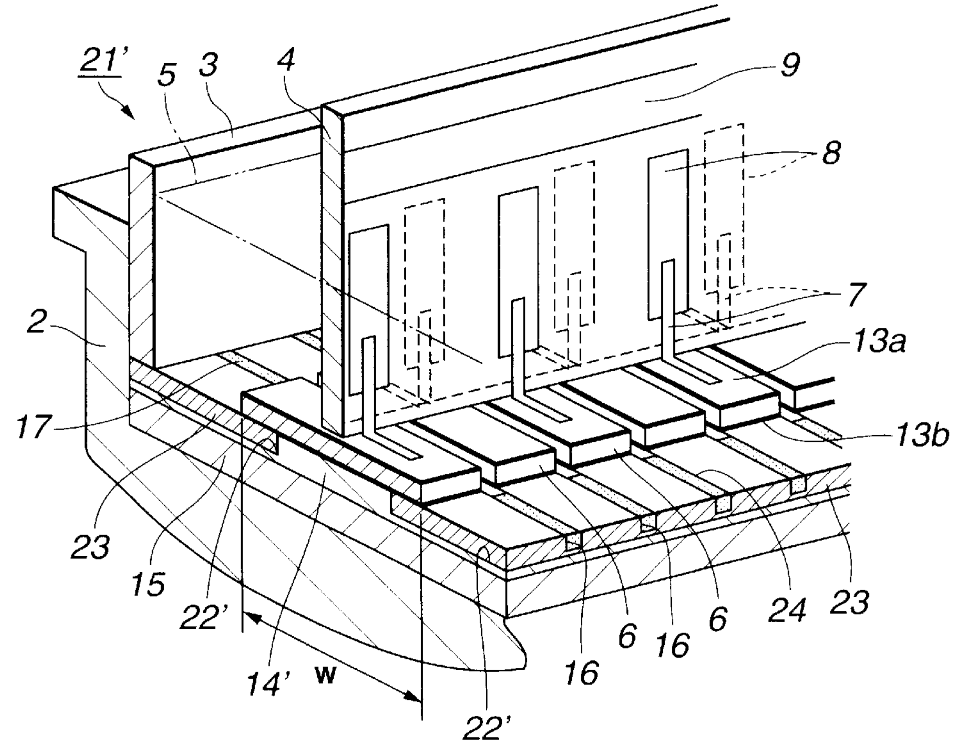
FIG. 6 is an explanatory diagram showing the internal structure of an ultrasound transducer array of a modification of the second aspect.

As a variant of the second aspect, a structure such as that shown in FIG. 6 may be adopted. In the ultrasound transducer array 21' shown in FIG. 6, the width of the groove portion 22 in FIG. 5 is effectively broadened (made larger) to extend to the edge of the first matching layer 14'. In other words, the central portion in the elevation direction of the first matching layer 14' is reserved, and both ends are cut away to form cut-out grooves 22', 22'; each cut-out groove 22' is filled with a conductive material to form the conductive layer 23.

Except near the portions in contact with the piezoelectric elements 6, each of the cut-out grooves 22' of the divided grooves 16 is filled with conductive adhesive 24. Otherwise the configuration is similar to that of FIG. 5, and the action and advantageous results are also similar.

In this aspect (including the variant), two conductive layers 23 are provided; however, either may be provided as the sole such layer instead.

Figure 7:
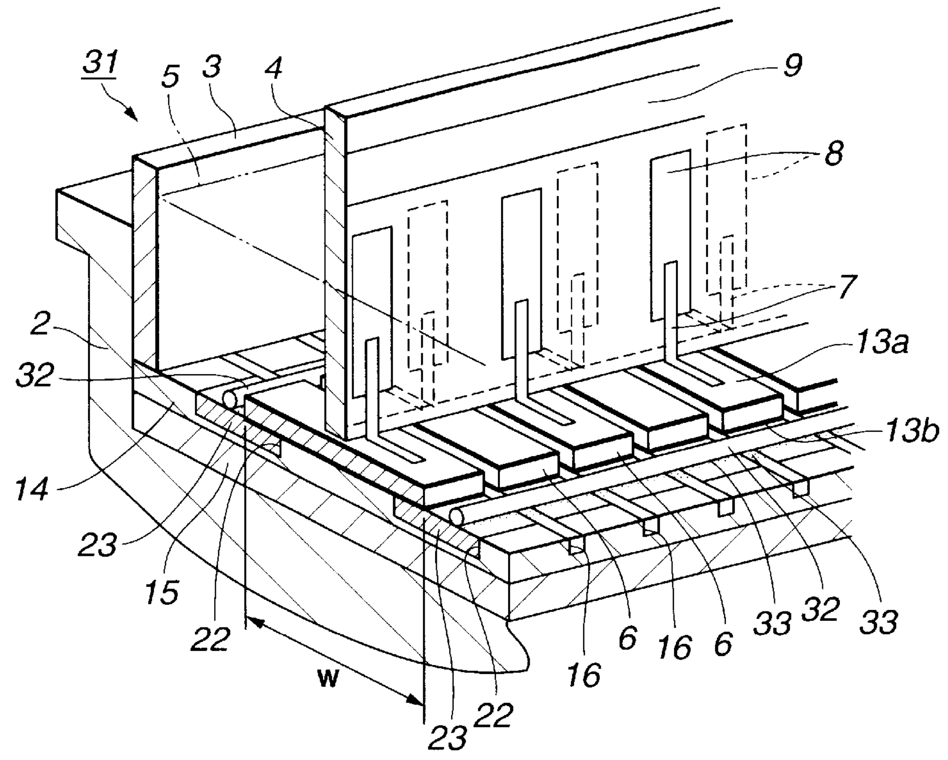
FIG. 7 is an explanatory diagram showing the internal structure of an ultrasound transducer array of a third aspect of the invention.

Next, the structure of the ultrasound transducer array of a third aspect of this invention is explained, referring to FIG. 7.

The ultrasound transducer array 31 of this aspect has a structure in which, after formation of the divided grooves 16 in the ultrasound transducer array 21 of FIG. 5, conductive wires 32, having common connection and reinforcement functions, are fixed with conductive adhesive 33 on the upper face of the portion of the conductive layer 23 not in contact with the piezoelectric elements 6, along the element array direction. The conductive wire 32 is formed of metal, for example silver.

The part of the divided grooves 16 near the lower side of the conductive wire 32 is filled with the conductive adhesive 33.

The effect and advantageous results of this aspect are substantially the same as in the case of FIG. 5; but by adopting the conductive wires 32, both the effect of common connection of the ground electrodes **13*b***, and the effect of reinforcement, can be enhanced.

Also, upon sterilizing the ultrasound transducer array 31 of this aspect in an autoclave, the resin part of the conductive layer 23 absorbs moisture and swells, and the electrical conductivity declines; but because the conductive wires 32 are metal wires, they are not affected by moisture and there is no decline in conductivity, so that durability with respect to sterilization can be improved.

Figure 8:
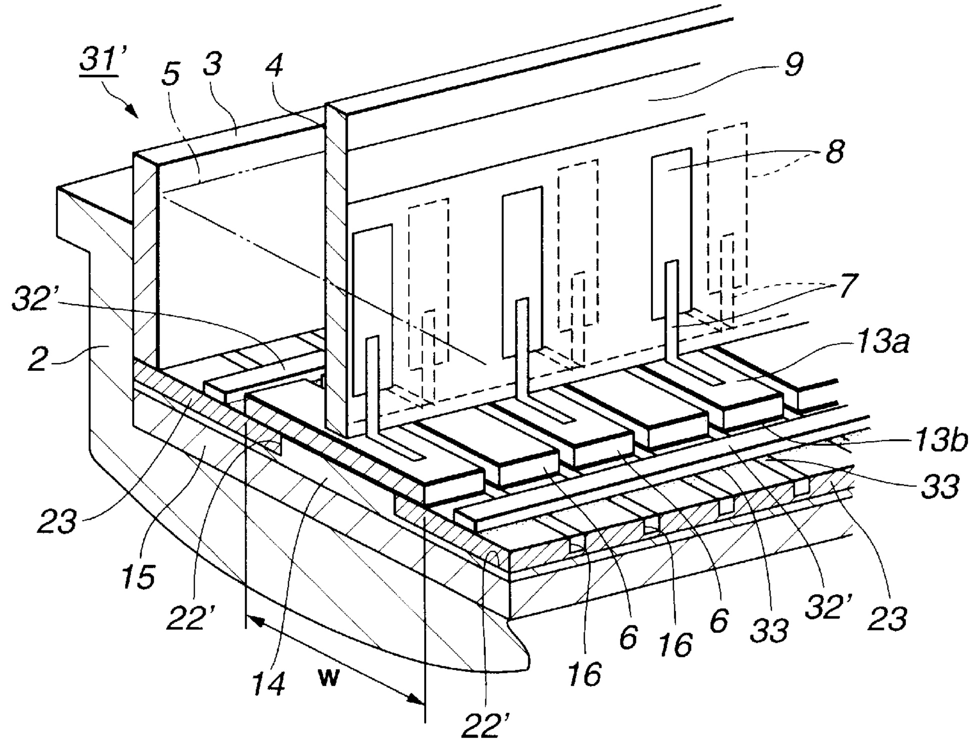
FIG. 8 is an explanatory diagram showing the internal structure of an ultrasound transducer array of a modification of the third aspect.

As a variant of this aspect, a structure such as that in FIG. 8 may be adopted. The ultrasound transducer array 31' shown in FIG. 8 has a structure in which, in the ultrasound transducer array 21' shown in FIG. 6, after forming the divided grooves 16 a flat wire 32' with rectangular cross-section for making a common connection is fixed with conductive adhesive 33 to the upper face of the portion of the conductive layer 23 not in contact with the piezoelectric elements 6, along the element array direction.

Of the divided grooves 16, the part near the lower part of this flat wire 32' is filled with conductive adhesive 33.

In this case also, the effect and advantageous results are similar to those of the above case.

In this aspect, including the variant, two wires 32 or flat wires 32' are provided; but a single wire only may be provided instead.

Figure 9:
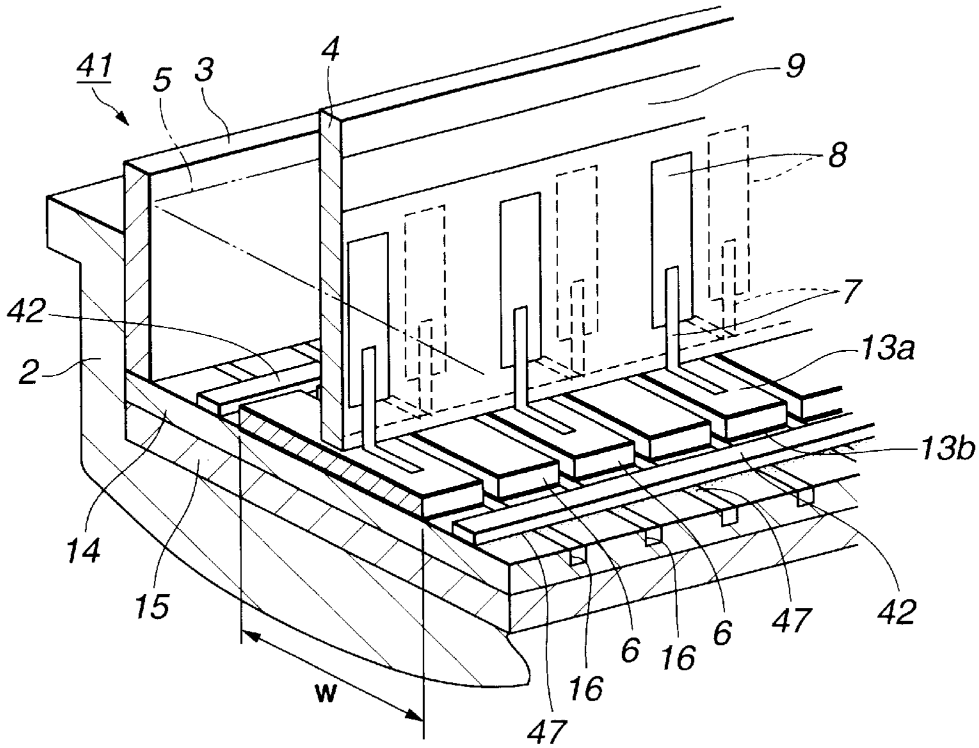
FIG. 9 is an explanatory diagram showing the internal structure of an ultrasound transducer array of a fourth aspect of the invention.

Next, the structure of the ultrasound transducer array 41 of a fourth aspect of this invention is explained, referring to FIG. 9.

This ultrasound transducer array 41 has a structure in which, in the ultrasound transducer array 1 of FIG. 4, after forming the divided grooves 16, conductive tape 42 for common connection is fixed with conductive adhesive 47 to the upper face of the portion of the first matching layer 14 not in contact with each piezoelectric element 6, along the element array direction. This conductive tape 42 is, for example, silver tape, on one face of which is provided an adhesive portion employing conductive adhesive 47.

Of the divided grooves 16, the portions near the bottom of this conductive tape 42 are filled with the conductive adhesive 47, to ensure more reliable conduction, and to provide a reinforcement function.

The effect and advantageous results of this aspect are substantially the same as in the cases of the aspects shown in FIG. 7 and FIG. 8.

Further, by employing conductive tape 42 as the conductive member for a common connection, mounting is simplified, and a larger contact area can be secured, so that a common connection of the ground electrodes can be made reliably, and manufacture of the ultrasound transducer array 41 becomes easier.

In this aspect, two conductive tape members 42 are provided, but a single tape member may be provided instead.

Figure 10:
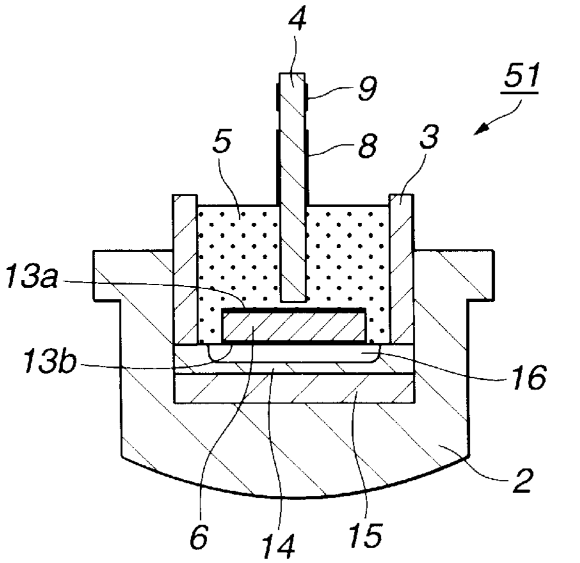
FIG. 10 is a cross-sectional view showing the structure of an ultrasound transducer array of a fifth aspect of the invention.

Next, a fifth aspect is explained, referring to FIG. 10. This figure shows a cross-section, along a dividing groove, of the structure of an ultrasound transducer array 51.

In this ultrasound transducer array 51, a dicing machine is used to form the divided grooves 16, similarly for example to the case of the ultrasound transducer array of the first aspect; but the divided grooves 16 are not formed extending to both ends of the first matching layer 14, but only in a portion which is extends slightly beyond both ends of the piezoelectric elements 6 (in the elevation direction).

That is, as shown in FIG. 10, divided grooves 16 are formed to separate the piezoelectric elements 6, and in addition the grooves are formed sufficiently deeply in the underlying first matching layer 14, in the portion opposed to the piezoelectric elements 6, to adequately suppress cross talk.

However, divided grooves 16 are not formed near both edges of the first matching layer 14, apart from the two edges, in the elevation direction, of the piezoelectric elements 6, and so the strength of the first matching layer 14 is increased compared with the case in which divided grooves 16 are formed in these portions as well; moreover, the occurrence of cracks during machining to form the divided grooves 16 can also be prevented.

In this aspect, divided grooves 16 are not formed in the portion (at both ends) of the first matching layer 14 apart from both ends in the elevation direction of the piezoelectric elements 6, and so this portion is not reinforced with filler material. Otherwise, the configuration is similar to that of the first aspect.

This aspect has substantially the same effect and advantageous results as the first aspect, even if the portion of the divided grooves 16 which is formed is not reinforced with conductive adhesive 17.

In FIG. 10, divided grooves 16 are formed in the vicinity adjacent to the piezoelectric elements 6, and divided grooves 16 are not formed at the two ends, thereby increasing the strength of the first matching layer 14; however, this aspect also includes a method in which the groove depth is reduced at both ends, to prevent reductions in strength.

This aspect has been explained as a variant of the first aspect with changes to the formed portions of the divided grooves 16; however, the changes can also be applied to the other aspects. That is, in the other aspects also, the divided grooves 16 may likewise be formed only in portions which are slightly longer than the piezoelectric elements 6.

Figure 11:
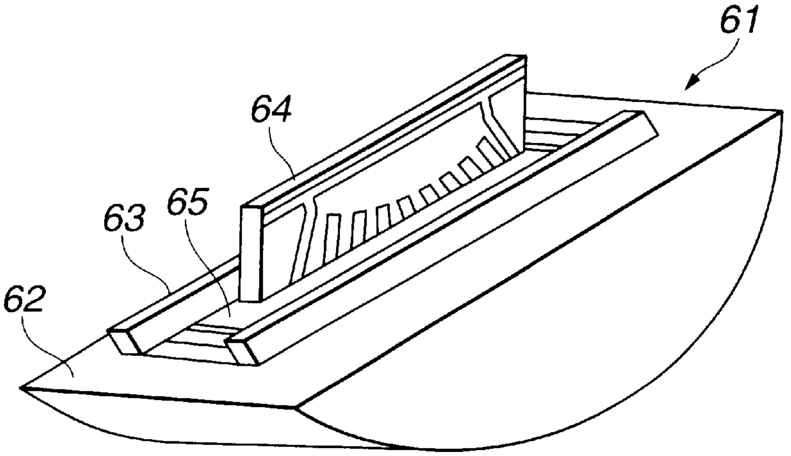
FIG. 11 through FIG. 13 relate to a sixth aspect of the invention.
Figure 12:
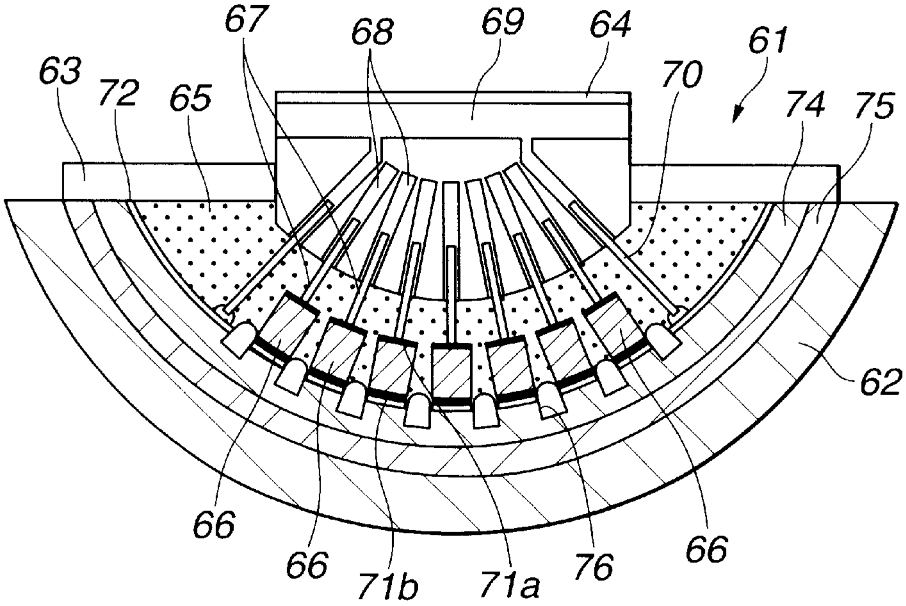
Figure 13:
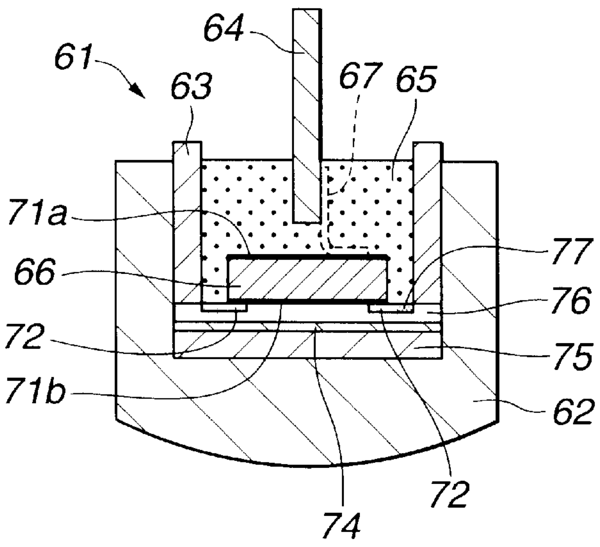

Next, a sixth aspect of this invention is explained, referring to FIG. 11 through FIG. 13. FIG. 11 shows the outer appearance of a curved linear-type ultrasound transducer array; FIG. 12 shows the cross-sectional structure in the element array direction; and FIG. 13 shows the cross-sectional structure in the elevation direction.

In this ultrasound transducer array, the backing material framework 63 is positioned inside the semicircular acoustic lens 62, the cable wiring board 64 is provided vertically inside this backing material framework 63, and the vicinity is filled with backing material 65.

On the cable wiring board 64 are provided signal wiring lands 68, 68, . . . , 68 almost radially in the length direction, being connected by signal wires 67 to a plurality of piezoelectric elements 66, 66, . . . , 66 formed in an array along, for example, a circular arc.

Near the upper portion of the cable wiring board 64, a GND wiring land 69 is formed in a strip shape in the length direction, and extends to ground wiring lands provided on both sides of the signal wiring lands 68, 68, . . . , 68. The ground electrodes 71*b* on the bottom side of the piezoelectric elements 66, 66, . . . , 66 are electrically connected, by means of solder or similar, to a conductive layer 72 using connecting wires 70.

As shown in FIG. 12 and FIG. 13, signal electrodes 71*a* and ground electrodes 71*b* are formed, by evaporation of metal or similar means, on the upper and lower faces of each piezoelectric element 66. On the bottom face, which performs transmission and reception of ultrasound, a first matching layer 74 and second matching layer 75 for matching, and an acoustic lens 62 for concentration of the emitted ultrasound, are formed in layers.

As shown in FIG. 13, grooves are formed on the upper face of the first matching layer 74 opposite both ends in the elevation direction of the piezoelectric element 66, and conductive layers 72 are formed in the grooves.

In this aspect, the first matching layer 14 is formed from, for example, epoxy resin.

The numerous piezoelectric elements 66, 66, . . . , 66 formed in an array are formed by providing full-coverage electrodes by evaporation deposition or similar on both faces of a belt-shape piezoelectric element board formed along a cylinder surface, bonding to this a first matching layer 74, and, by using a dicing machine to form divided grooves 76 so as to separate elements, forming an array of elements separated in the array direction along the cylinder surface.

Except for the portion adjacent to the piezoelectric elements 66, the portion of each dividing groove 76 in which is formed a conductive layer 72 is filled with a conductive filler material 77, for common connection to the ground electrodes 71*b* and for reinforcement.

Except for the fact that ultrasound is transmitted and received radially, this aspect has substantially the same effect and advantageous results as the first aspect.

In each of the above-described aspects, it is preferable that the divided grooves be deep rather than shallow, in consideration of the effect of cross talk. Also, in the above-described aspects a matching layer is formed from a first matching layer and a second matching layer; however, a single matching layer may be used or, three or more matching layers may be used.

Aspects which are configured by partial combination of the above-described aspects or similar, also, fall within the scope of this invention.

The above has mainly explained the structure of ultrasound transducers. The following explanation places emphasis on selection of materials.

Figure 30A:
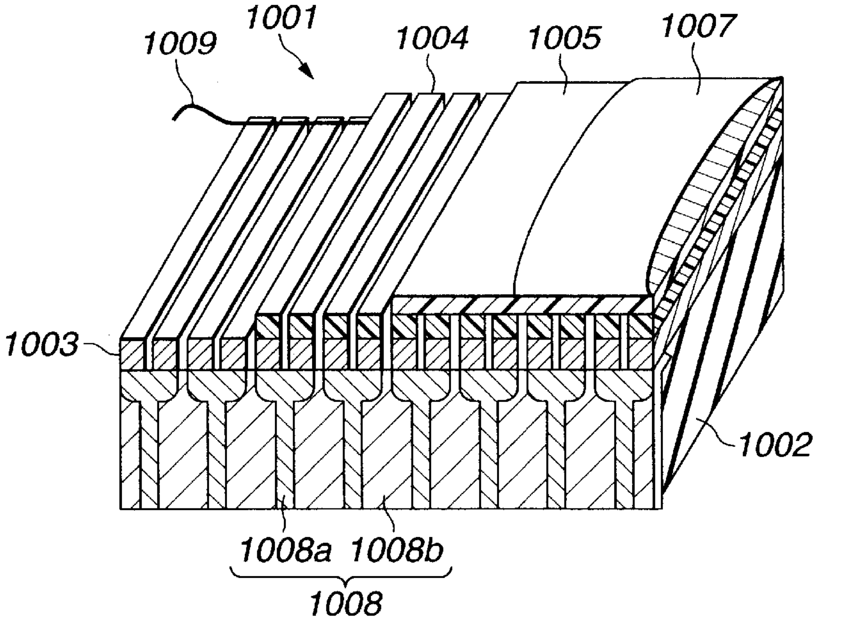
FIG. 30A is a summary perspective view showing the configuration of an ultrasound transducer array.
Figure 30B:
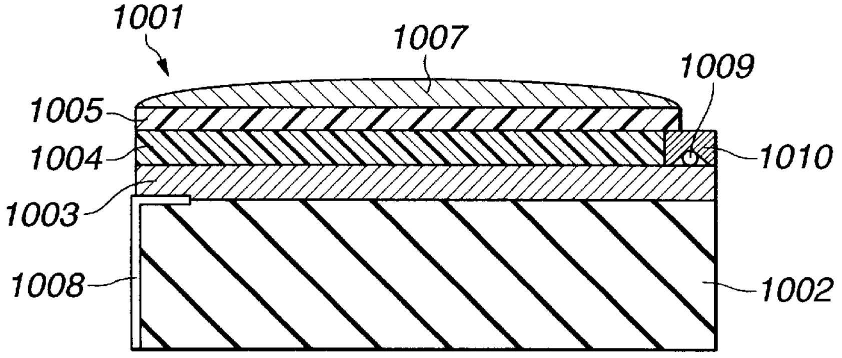
FIG. 30B is a side cross-sectional view of FIG. 30A.

Japanese Unexamined Patent Application Publication No.9-139998 discloses an ultrasound transducer array having a back load member, piezoelectric elements, matching layer comprising carbon as a conductive material, and acoustic lens, with these layered in order similarly to the ultrasound transducer array 1001 shown in FIG. 30A and FIG. 30B. The matching layer is joined, with electrical conductivity ensured, to electrodes formed on the upper faces of the piezoelectric elements. The matching layer also serves as a grounding electrode.

Japanese Patent Publication No.1-61062 discloses an ultrasound transducer array having a back load member, piezoelectric elements, and matching layer comprising conductive resin as a conductive material, with these layered in order. The conductive resin is formed by intermixing metal powder as a filler into a resin material as a matrix. Similarly to Japanese Unexamined Patent Application Publication No.9-139998, the matching layer is used as a ground electrode.

However, in the ultrasound transducer array of Japanese Unexamined Patent Application Publication No.9-139998 using carbon in the matching layer, whereas the matching layer has electrical conductivity and good cutting properties, while when the thickness typically used for the matching layer is (¼)λ, mechanical strength is reduced, and cracks and chips appear during machining into thin sheets.

In cases where uncombined carbon is used to form the matching layer, when the ultrasound transducer array is used with the human body, the acoustic impedance of the acoustic impedance-matching layer deviates from the optimal value. As a result, ultrasound is not propagated efficiently, sensitivity declines, and image definition deteriorates.

In the ultrasound transducer array of Japanese Patent Publication No.1-61062, using conductive resin for the matching layer, by appropriately choosing the filler material and the resin material as the matrix, electrical conductivity can be obtained; but in addition to aging, during such processes as disinfecting and sterilization, the disinfectant and sterilizing fluids may penetrate into the resin and cause degradation or swelling of the resin, or oxidation or other changes to the metal filler, worsening electrical conductivity and increasing the resistance value. As a result the S/N ratio decreases, and conduction faults and image quality deterioration occur. Also, the conductive resin is a material with large ultrasound attenuation factor, so that transmission and reception sensitivity and image quality are reduced.

Hence there is a need for an ultrasound transducer array comprising a matching layer which is conductive, not prone to cracking or chipping during machining, which is easy to machine, and has an optimal acoustic impedance.

Below, seventh to thirteenth aspects of this invention are explained, referring to FIG. 14 through FIG. 23.

Figure 14:
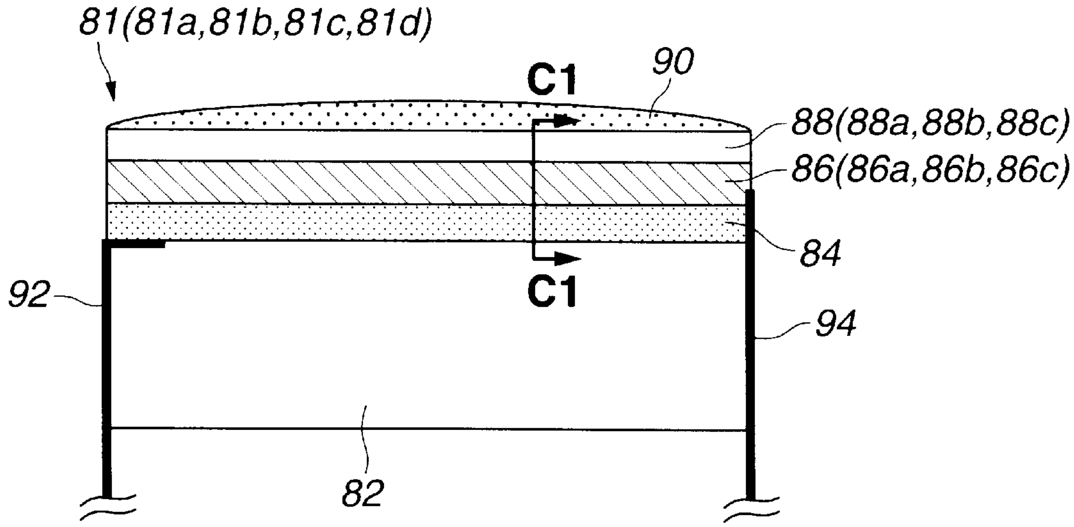
FIG. 14 through FIG. 17 relate to a seventh aspect of the invention.
Figure 15:
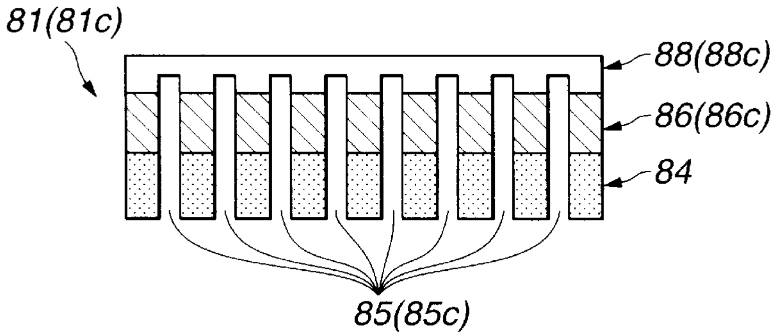
Figure 16:
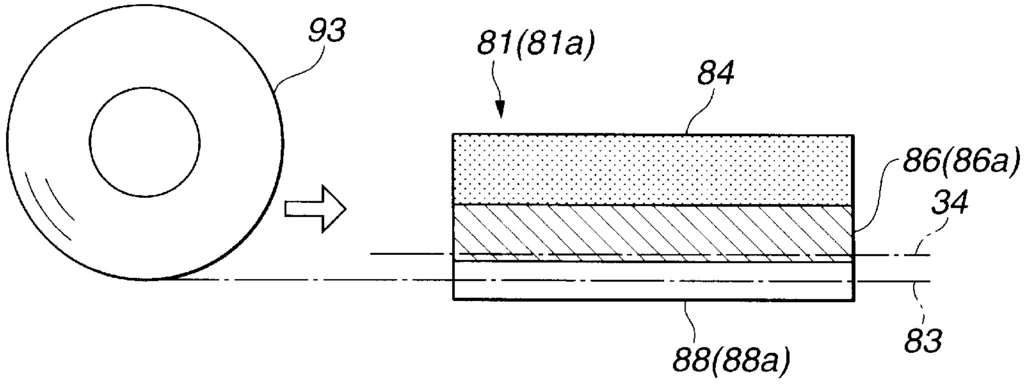
Figure 17:
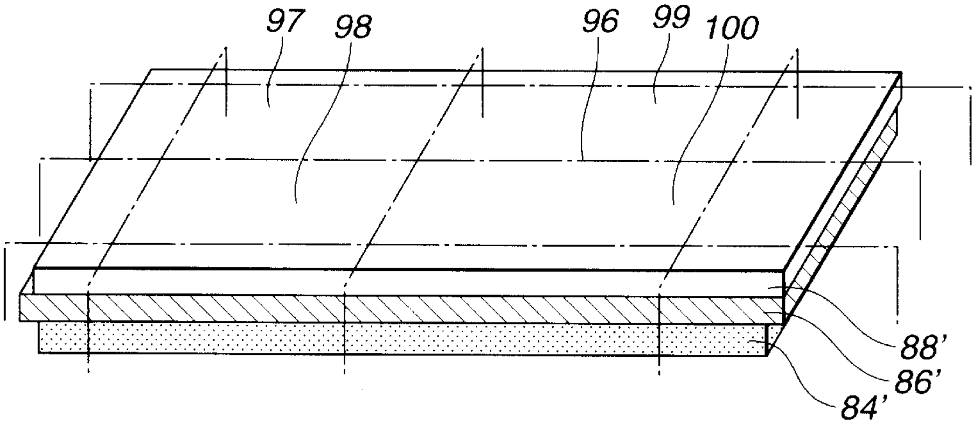

FIG. 14 through FIG. 17 show the seventh aspect of this invention. FIG. 14 is a side view of an ultrasound transducer array; FIG. 15 is a cross-sectional view of a layered member, cut along line C1—C1 in FIG. 14; FIG. 16 is a side view of the layered member of an ultrasound transducer array manufactured by a first manufacturing method; and FIG. 17 is a perspective view of the principal components of the parent layered member of an ultrasound transducer array manufactured by a second manufacturing method.

The ultrasound transducer array 81 of this aspect has a back load member 82. The back load member 82 is formed from a flexible urethane resin, with alumina used as a filler. The urethane resin has a Shore hardness of approximately A90.

In FIG. 14, the front surface of the back load member 82, which is one of the four surfaces, faces the plane of the paper. On the upper surface of the back load member 82 are layered, in the order of a piezoelectric element 84, first matching layer 86, and second matching layer 88. The piezoelectric element 84 is formed from a piezoelectric ceramic manufactured by ordinary sintering processes or similar.

Electrodes are formed on the lower surface (the surface opposed to the upper surface of the back load member 82) and the upper surface of the piezoelectric element 84. The first matching layer 86 comprises a carbon composite material containing carbon, and is conductive.

A conductive layer (not shown) provided at the portion of this first matching layer 86 which is in contact with both ends in the elevation direction of the piezoelectric element 84 is formed by intermixing carbon powder with a thermosetting resin matrix. This carbon powder may be the same as the powder of the carbon composite material used to form the first matching layer 86. The thermosetting resin may be a material which hardens at room temperature.

The thickness of the first matching layer 86 is 200 $\mu$m, and when using 5 MHz ultrasound, the ultrasound is propagated efficiently. The second matching layer 88 is formed from an epoxy resin, and is of thickness 100 $\mu$m. The piezoelectric element 84, first matching layer 86 and second matching layer 88 form a layered member.

In FIG. 16, the front surface (the surface facing the plane of the paper in FIG. 14) of the layered member is facing the plane of the paper, and the top and bottom are reversed from their positions in FIG. 14. The lower surface of the layered member is the lower surface of the piezoelectric element 84. On the layered member are formed a plurality of array grooves 85, extending along the lower surface of the layered member. These array grooves 85 extend substantially parallel to the front surface of the layered member and in substantially straight lines, and are positioned at prescribed intervals.

As shown in FIG. 16, the array grooves 85 are formed between the lower surface of the piezoelectric element 84 (the surface in contact with the back load member 82) and a line 83 passing through the second matching layer 88. Through formation of the array grooves 85, the piezoelectric element 84 and first matching layer 86 are each divided into a plurality of portions. Focusing on the first matching layer 86, the array grooves 85 extend along the surface of the first matching layer 86, and the depth of each dividing groove 85 is, at all portions of the dividing groove 85, equal to the thickness of the first matching layer 86, such that the first matching layer 86 is divided. An acoustic lens 90 is provided on top of the second matching layer 88 (FIG. 14). The acoustic lens 90 is formed from silicone resin. The upper surface of the acoustic lens 90 is formed in a convex shape.

In the back load member 82, a substantially flat flexible printed board 92 extends in the vertical direction along a side surface adjacent to the front surface. The top end of the flexible printed board 92 is enclosed between the upper surface of the back load member 82 and the lower surface of the piezoelectric element 84. The other hand is connected to a pulser and observation equipment, not shown, similarly to the conventional ultrasound transducer array 1001 shown in FIG. 30A and FIG. 30B.

A plurality of lead wires are positioned on the flexible printed board 92. These lead wires are connected, via solder, to electrodes on the lower surface of corresponding portions of the divided piezoelectric elements 84. The flexible printed board 92 is used as signal lines to transmit driving signals and received signals.

In the ultrasound transducer array 81, a substantially flat flexible printed board 94 having a full-coverage electrode is bonded with conductive adhesive to the side surface opposite the side surface on which the flexible printed board 92 is provided. The piezoelectric element 84 and first matching layer 86 are electrically connected, and by bonding the flexible printed board 94 to the first matching layer 86, the first matching layer 86 forms a common electrode for each of the portions of the divided piezoelectric element 84.

A polyimide insulator is positioned on the portion of the flexible printed board 94 adjacent to the piezoelectric element 84. By this means, the electrode on the lower surface of the piezoelectric element 84 is insulated from the flexible printed board 94. The flexible printed board 94 is connected to ground, not shown, and used as a ground line.

As described above, the electrode on the upper surface of the piezoelectric element 84 is connected to the first matching layer 86 and to ground via a ground line. The action of the ultrasound transducer array 81 is similar to that of the ultrasound transducer array 1001 of FIG. 30A and FIG. 30B, and an explanation is here omitted.

Next, the material forming the first matching layer 86 is explained. As described above, the first matching layer 86 is formed from a carbon composite material. This carbon composite material contains carbon and carbides. These carbides contain silicon carbide (SiC) and boron carbide ($B_4C$). The above carbon composite material contains fine ceramic powder of these carbides, and fine ceramic powder of borides. The carbon composite material is formed into sintered members.

The strength of the first matching layer 86 comprising this carbon composite material is higher compared with a layer comprising carbon alone. This is thought to arise by the following reasons.

The carbon composite material is formed primarily from granular carbon and from fine ceramic particles existing between the carbon grains. The fine ceramic particles are embedded like wedges between adjacent carbon grains. By this means, adjacent carbon grains are not easily separated by fine ceramic particles, so that the growth of microcracks is believed to be suppressed. In particular, when the shape of the fine ceramic particles is polygonal having protrusions and depressions (a combination of polygons) rather than spherical, there is a strong action binding carbon grains in place, and strength can be expected to be improved.

In this way, there is little occurrence of cracking and chipping during machining of the carbon composite material, so that machining is relatively easy. Particularly when used with high-frequency ultrasound at 10 MHz or more, the matching layer must be machined to a thickness of 100 μm or less, but this machining to a thin shape can also be performed easily.

The carbon composite material is formed by intermixing carbon with silicon carbide (SiC) having an average particle diameter of 0.5 μm and boron carbide ($B_4C$) having an average particle diameter of 5 μm. The mass fractions of the silicon carbide (SiC) and of the boron carbide ($B_4C$) are respectively 6 wt % (mass percentage) and 9 wt %. In addition to these, 4 wt % zirconium boride is also intermixed with the carbon. The acoustic impedance is approximately $8.5\times10^6$ kg/m$^2$s (8.5 MRayl).

The carbon composite material contains fine ceramic particles of density higher than carbon, so that compared with uncombined carbon, the density is higher. Consequently the acoustic impedance of the carbon composite material is larger than that of uncombined carbon.

If the proportion of carbides intermixed in the carbon composite material (that is, the mass fraction) is changed, or the average grain diameter is varied, the acoustic impedance changes. Typically, acoustic impedances between approximately $7.5\times10^6$ kg/m$^2$s (7.5 MRayl) and approximately $10\times10^6$ kg/m$^2$s (10 MRayl) can be obtained. By this means, a matching layer which has optimal acoustic impedance can be prepared for the efficient propagation of ultrasound.

In the case of a resin formed with a filler intermixed in the resin material, if the intermixed filler is modified, the acoustic impedance also changes. However, such a resin has a large ultrasound attenuation factor, so that if a matching layer using such a resin is employed, the ultrasound is not propagated efficiently. In particular, a conductive resin such as that disclosed in Japanese Patent Publication No.1-61062 contains a filler with a unique shape in order to secure conductivity, and for this reason has a still larger attenuation factor, so that this defect is more prominent. Compared with such a resin, a carbon composite material has a comparatively small ultrasound attenuation factor, and so ultrasound propagates comparatively efficiently. In this way, by using a matching layer consisting of a carbon composite material, a stronger driving signal can be guided to the object, and a stronger received signal can be made incident on the piezoelectric element. Hence the sensitivity of the ultrasound transducer array 81 can be improved.

In this aspect, the carbon composite material is formed by mixing silicon carbide (SiC), boron carbide ($B_4C$) and zirconium boride into carbon; but a similar advantageous result to that of the carbon composite material of this aspect is obtained from a carbon composite material in which, in place of mixing the above compounds with carbon, aluminum carbide ($Al_4C_3$) and other carbides, and tungsten boride (WB) and similar, are mixed with carbon. Also, an advantageous result similar to that of the carbon composite material of this aspect is also obtained if at least one among silicon carbide (SiC), boron carbide ($B_4C$), zirconium boride, aluminum carbide ($Al_4C_3$), and tungsten boride (WB), is intermixed.

In an ultrasound transducer array 81 with such a configuration, by varying the ratio of silicon carbide (sic) and boron carbide ($B_4C$), the acoustic impedance of the carbon composite material can be modified, and so an ultrasound transducer array 81 can be provided comprising a matching layer having an optimal acoustic impedance.

Further, because the carbon composite material does not swell due to moisture or water as resins do, this material can be durable even for transducers subjected to harsh washing or requiring sterilization for use within the body.

Of course various modifications and alterations of the configurations of this aspect are possible. When using 5 MHz ultrasound, the thickness of the first matching layer 86 is 200 μm; but this invention is not limited to this thickness. For example, in order to use 10 MHz ultrasound, the thickness may be made 100 μm. Also, in order to use ultrasound with an arbitrary frequency, it is of course possible that the thickness can correspond to the frequency.

In this aspect, by providing an insulator on the surface of the flexible printed board 94 facing the piezoelectric elements 84, the flexible printed board 94 is insulated from the electrodes on the lower surface of the piezoelectric elements 84; however, this invention is not limited to this configuration. For example, insulation may be effected by forming the electrodes on the lower surface of the piezoelectric elements 84 such that the electrodes on the lower surface of the piezoelectric elements 84 are not exposed to the outside from a crevice between a side surface of the piezoelectric elements 84 and a side surface of the first matching layer 86. The portion of the electrodes on the lower surface of the piezoelectric elements 84 which are exposed to the outside may be insulated by sealing with resin.

In this aspect, the flexible printed board 92 is connected to the electrodes of the piezoelectric elements 84 via solder; but this invention is not thereby limited. For example, connection may be made by an anisotropic conductive film (ACF). In this case, depolarization of piezoelectric elements 84 arising from contact of the piezoelectric elements 84 with heated solder can be prevented.

The piezoelectric elements 84 may be curved in a convex shape in a direction intersecting the direction in which the array grooves 85 extend. Such an ultrasound transducer array 81 is called a convex-array probe.

Next, method of manufactures of the ultrasound transducer array 81 of this aspect is explained. Two methods of manufacture of the ultrasound transducer array 81 are conceivable.

Initially, a first manufacturing method is explained.

First Process:

Carbon composite material containing prescribed carbides is prepared, and this carbon composite material is ground to shape a substantially flat first matching layer 86.

As explained above, the thickness of the first matching layer 86 is 200 μm. In order to shape carbon composite material to a thickness of 200 μm, a two-sided lapping machine may be used, or wax or a water-soluble adhesive may be used to apply the carbon composite material to a base, and grinding and polishing performed to machine the carbon composite material.

Second Process (process of formation of the second matching layer):

A framework is mounted so as to cover the side faces of the first matching layer 86, forming a container, and tape or similar is used to mask one surface of the first matching layer 86.

A water-soluble resin or resist may be used for masking. The bottom face of this container is the first matching layer 86; the side faces constitutes the framework. The masked surface is the surface facing outside the container.

Next, epoxy resin is poured into the container, and the resin is hardened to form the second matching layer 88. The amount of resin poured is adjusted such that the thickness of the second matching layer 88 is 100 μm. Then the framework and masking are removed.

Third Process (process to form a layered member):

A piezoelectric element 84 which is substantially flat and with electrodes formed on the upper and lower surfaces is prepared. The upper surface of the piezoelectric element 84 is bonded with adhesive to the surface of the first matching layer 86 from which the masking was removed, to form a layered member comprising the piezoelectric element 84, first matching layer 86, and second matching layer 88.

Fourth Process (process to connect signal lines):

The flexible printed board 92, serving as signal lines, is connected via solder to the electrode on the bottom surface of the piezoelectric element 84 (the reverse side surface of the surface in contact with the first matching layer 86).

Fifth Process (process to form array grooves):

As shown in FIG. 16, the blade 93 of a precision cutting machine is moved from one side surface adjacent to the front surface of the layered member to the other side surface, along a line 83 in the direction of the arrow in the figure. As explained above, the line 83 penetrates the second matching layer 88. By repeating this movement, the array grooves 85 shown in FIG. 15 are formed.

Sixth Process:

Using a framework similar to that of the second process, the back load member 82 is formed using urethane resin on the bottom surface of the piezoelectric elements 84.

Next, conductive adhesive is used to bond the flexible printed board 94, serving as a ground line, to the side surface of the first matching layer 86. Then, silicone resin is used to form an acoustic lens 90 on the upper surface (the reverse side surface of the surface in contact with the first matching layer 86) of the second matching layer 88.

As described in detail above, in the first method of manufacture of the ultrasound transducer array 81, there is little occurrence of cracking or chipping during machining, and by using easily-machined carbon composite material as the first matching layer 86, manufacturing can be performed easily.

In the first process of this first manufacturing method, in order to enable the use of 5 MHz ultrasound, the carbon composite material is ground to form a first matching layer 86 of thickness 200 $\mu$m. However, in order to use ultrasound at still higher frequencies, the carbon composite material may be machined to a thinner shape. In this case, because the carbon composite material is such that cracking and chipping do not readily occur during machining, machining can be performed more easily than the machining to a thin shape of uncombined carbon such as is used in the matching layer of Japanese Unexamined Patent Application Publication No.9-139998.

It is preferable that the content of fine ceramic powder including carbides in the carbon composite material used as the matching layer of this invention be from 10 to 50 wt %. If 50 wt % or more is intermixed, electrical conductivity worsens, and because of the high hardness of the carbides such as SiC and $B_4C$ which are intermixed to suppress microcracks, the lifetime of grinding tools used in machining is shortened, and as a result it becomes difficult to reduce the cost of the probe. If the content is 10 wt % or less, the effect in suppressing microcracks is reduced. It is preferable that the carbon composite material be sintered and bake-hardened.

In order to manufacture a convex-array probe, the layered member may be curved in a convex shape. The second matching layer 88 is formed from epoxy resin, and is flexible. By using this to deform the vicinity of the array grooves 85 in the second matching layer 88 after forming the layered member of FIG. 15, a convex-array probe can be manufactured.

Next, a second method of manufacture of the ultrasound transducer array 81 is explained. The above-described first manufacturing method and the second manufacturing method are essentially the same.

Differences between the first manufacturing method and the second manufacturing method are the provision of a process to cut the layered member between the third process (process to form the layered member) and the fourth process (process for signal line connection) of the first manufacturing method.

The layered member (parent layered member) is formed according to the first through third processes (layered member formation processes) of the first manufacturing method, and in the next process, the blade 93 of a precision cutting machine is used to cut the unmachined layered member (parent layered member) along the lines 96.

As in FIG. 17, lines 96 in a lattice shape show the portions of the parent layered member to be cut. The surface of the parent layered member is larger than four times the surface of the layered member formed according to the first manufacturing method.

The parent layered member has a piezoelectric element 84' which is effectively the same as the piezoelectric element, first matching layer and second matching layer formed in the first manufacturing method; a first matching layer 86'; and a second matching layer 88'. There exist four windows in the lines 96 in a lattice shape. When the parent layered member is cut along the lines 96, four layered members (child layered members) 97, 98, 99, 100 corresponding to the four windows of the lattice are obtained. The remaining portions of the parent layered member are discarded.

Then, by performing the fourth process (process to connect signal lines) and subsequent processes of the above first manufacturing method, the ultrasound transducer array 81 shown in FIG. 14 is obtained.

In the above-described first manufacturing method, the side surfaces of the layered member formed in the third process (process to form the layered member) and previous processes may be smeared with epoxy resin leaked from the framework of the second process (process to form the second matching layer) or with the adhesive used in the third process (process to form the layered member).

However, in the second manufacturing method, the portions which had been in contact with the side surfaces of the parent layered member are discarded after cutting, so that the side surfaces of the child layered members are not smeared. Hence in the sixth process, the flexible printed board 94 can be bonded to the side surface of a child layered member free of smearing, and so there is no intervening adhesive or other insulator. Thus reliability is improved when securing electrical conductivity at the side surface of the carbon composite material. Also, the contact strength and bonding durability can be improved.

The time required to form four child layered members through this manufacturing method is approximately ¼ the time required to form four layered members through the above-described first manufacturing method. By means of this manufacturing method, ultrasound transducer arrays 81 can be manufactured rapidly and at low cost.

In this aspect, the layered member is cut along the lines 96 in a lattice shape having four windows; but this invention is not thus limited. The number of windows may be two or three, or may be five or more. Also, the window shape is not limited to a quadrilateral, but may for example be a hexagon. Also, the method for cutting the layered member is not limited to a lattice.

Figure 18:
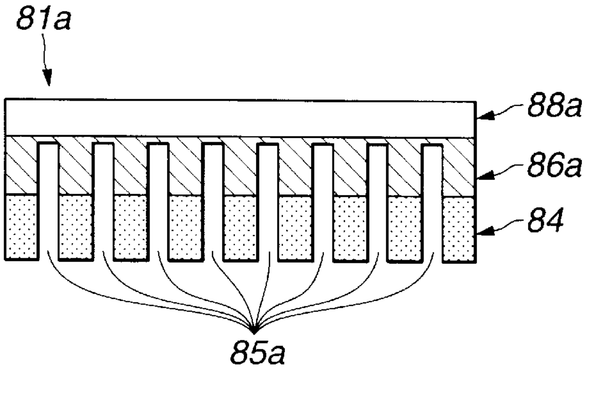
FIG. 18 is a cross-sectional view of an ultrasound transducer array of an eighth aspect of the invention.

FIG. 18 shows a cross-sectional view of the ultrasound transducer array of an eighth aspect of this invention. The configuration of the ultrasound transducer array 81*a* of this aspect is basically the same as that of the ultrasound transducer array 81 of the seventh aspect, and the configuration as seen from the front of the ultrasound transducer array 81 is the same as in the seventh aspect; hence an explanation is given referring to FIG. 14 as a side view of the ultrasound transducer array 81*a* of this aspect, and to FIG. 16 as a side view of the layered member of this aspect.

Differences between the configuration of this aspect and the configuration of the seventh aspect; hence in FIG. 14 and FIG. 16, the first matching layer is indicated by the symbol 86*a* instead of the symbol 86, and the second matching layer is indicated by the symbol 88*a* instead of the symbol 88.

FIG. 18 is a cross-sectional view of the layered member, along the line C1—C1 in FIG. 14. In the layered member of the seventh aspect shown in FIG. 15, the array grooves 85 are formed from the lower surface of the piezoelectric elements 84 to the second matching layer 88, but in the layered member shown in FIG. 18, the array grooves 85*a* are only formed up to the first matching layer 86*a*.

Referring to FIG. 16 and FIG. 18, the array grooves 85*a* are formed between the lower surface of the piezoelectric elements 84 and the line 34 penetrating the first matching layer 86*a*. Concerning the first matching layer 86*a*, the depth of the array grooves 85*a* is, throughout the entirety of the array grooves 85*a*, less than the thickness of the first matching layer 86*a*.

In the eighth aspect of an ultrasound transducer array 81*a* configured as described in detail above, the first matching layer 86*a* is not divided by the array grooves 85*a*, so that by connecting wires to a part of the conductive first matching layer 86*a*, an electrical connection is made entirely to the divided portions of the first matching layer 86*a*. Hence the flexible printed board 94 used as a ground line need not be bonded to all divided portions of the first matching layer 86*a*. Bonding to at least one portion of the first matching layer 86*a* is sufficient, and so a highly reliable ultrasound transducer array 81 with simple configuration can be provided.

The ultrasound transducer array 81*a* of this aspect can, in essence, be manufactured by either the first or the second method for manufacturing the ultrasound transducer array 81 of the above-described seventh aspect. However, in the fifth process (process to form array grooves), the blade 93 of the precision cutting machine is moved along the lines 34 rather than along the lines 83.

Figure 19:
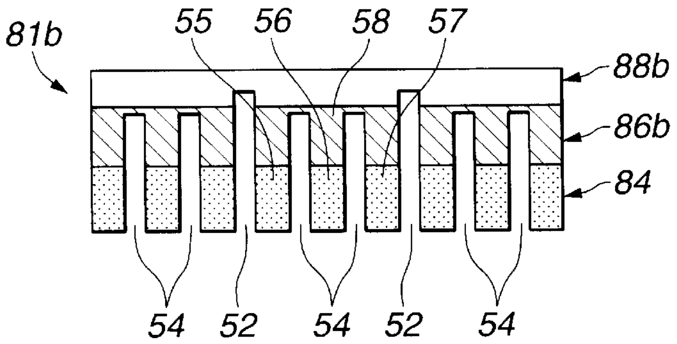
FIG. 19 is a cross-sectional view of an ultrasound transducer array of a ninth aspect of the invention.

FIG. 19 shows a cross-sectional view of the ultrasound transducer array of a ninth aspect of this invention. The configuration of the ultrasound transducer array 81*b* of this aspect is essentially the same as the configuration of the ultrasound transducer array 81 of the seventh aspect.

The configuration seen from the front of the ultrasound transducer array 81*b* of this aspect is the same as that of the seventh aspect, and so FIG. 14 is again referenced as a side view of the ultrasound transducer array 81*b* of this aspect.

Differences in the configuration of this aspect and the configuration of the seventh aspect are the configurations of the first matching layer and the second matching layer; hence in FIG. 14, the first matching layer is indicated by the symbol 86*b* instead of the symbol 86, and the second matching layer is indicated by the symbol 88*b* instead of the symbol 88. FIG. 19 is a cross-sectional view of the layered member along the line C1—C1 in FIG. 14.

The array grooves 85 of the seventh aspect shown in FIG. 15 and FIG. 16 are formed up to the line 83 penetrating the second matching layer 88. However, the array grooves 85*a* shown in FIG. 16 and FIG. 18 are formed up to the line 34 passing through the first matching layer 86*a*. Different from the layered member of the seventh aspect, in the layered member of the ninth aspect there are regularly intermixed main dicing grooves 52, which are grooves of depth similar to the array grooves 85, and sub-dicing grooves 54, which are grooves of depth similar to the array grooves 85*a*, as shown in FIG. 19. If the main dicing grooves 52 are abbreviated "deep" and the sub-dicing grooves 54 are abbreviated "shallow", then these grooves are arranged in the order "shallow", "shallow", "deep", "shallow", "shallow", "deep", "shallow", "shallow", with two sub-dicing grooves 54 isolated by main dicing grooves 52.

As a result, the portions of the piezoelectric element 84 divided by the main dicing grooves 52 are further separated into three portions by the two sub-dicing grooves (for example, the portions 55, 56, 57). On the other hand, in the portion 58 of the first matching layer 86*b* separated by main dicing grooves 52, sub-dicing grooves 54 are formed, but this portion 58 is not divided, and remains continuous. The portions 55, 56, 57 of the piezoelectric element 84 are mutually electrically connected via the portion 58 of the first matching layer 86*b*. The portions 55, 56, 57 and the portion 58 form a single driving unit. The layered member has a plurality of such driving units.

In the seventh aspect, the flexible printed board 94 must be bonded to all portions of the divided first matching layer 86. In an ultrasound transducer array 81*b* configured as described in detail above, the flexible printed board 94 need only be bonded to one portion of each driving unit, so that reliability with respect to electrical conduction faults can be improved. Further, the portions of the piezoelectric element 84 forming driving units are further divided by the sub-dicing grooves 54, so that the sensitivity of the ultrasound transducer array 81*b* can be improved.

In this aspect, two sub-dicing grooves 54 are isolated by main dicing grooves 52; however, the present invention is not thus limited. For example, single sub-dicing groove may be isolated by main dicing grooves; or, three or more sub-dicing grooves may be so isolated.

The piezoelectric elements 84 may be curved in a direction intersecting the direction in which the main dicing grooves 52 extend. Utilizing the fact that the second matching layer 88*b* is flexible, by deforming the second matching layer 88*b* near the main dicing grooves 52, and arranging the driving units in a convex shape, a convex-array probe can be formed.

The ultrasound transducer array 81*b* of this aspect can in essence be manufactured by either the first or the second method of manufacturing the ultrasound transducer array 81 of the above-described seventh aspect. However, in the fifth process (the process to form the array grooves), the blade 93 of the precision cutting machine is moved along the line 83 or the line 34 in order to form the main dicing grooves 52 or the sub-dicing grooves 54, respectively.

Figure 20:
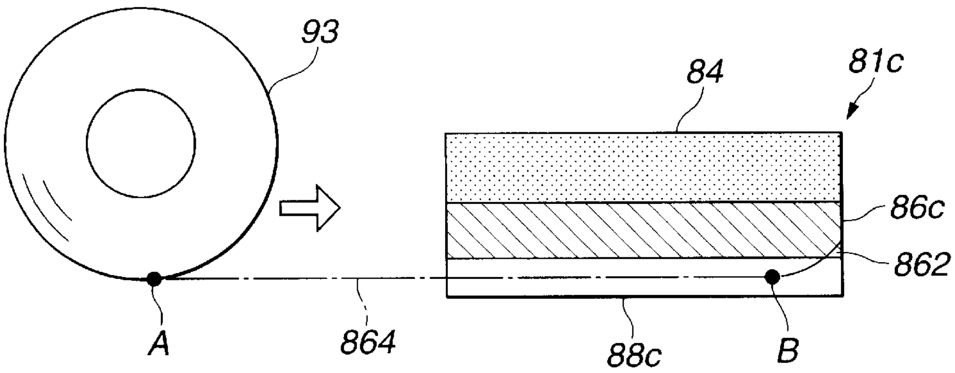
FIG. 20 is a side view of the layered member of an ultrasound transducer array of a tenth aspect of the invention.

FIG. 20 is a side view of the layered member of the ultrasound transducer array of a tenth aspect of this invention. The configuration of the ultrasound transducer array 81*c* of this aspect is essentially the same as the configuration of the ultrasound transducer array 81 of the seventh aspect. The configuration as seen from the front of the ultrasound transducer array 81*c* of this aspect is the same as that of the seventh aspect, and so FIG. 14 is again referenced as a side view of the ultrasound transducer array 81*c* of this aspect.

Also, the configuration of the layered member of this aspect as seen along the line C1—C1 of FIG. 14 is the same as that of the seventh aspect, and so FIG. 15 is again referenced as a cross-sectional view of the layered member of this aspect.

Differences between the configuration of this aspect and that of the seventh aspect are the configurations of the first and the second matching layers; hence in FIG. 14 and FIG. 15, the first matching layer, second matching layer, and array grooves are indicated by the symbols 86*c*, 88*c* , 85*c* instead of the symbols 86, 88, 85, respectively.

In FIG. 20, similarly to FIG. 16, the front surface of the layered member faces the plane of the paper, and the top and bottom are reversed relative to FIG. 14. In the seventh aspect, the bottom surfaces of the array grooves 85 are along a line 83 which penetrates the second matching layer 88, as shown in FIG. 16; but in this aspect, the bottom surfaces of the array grooves 85*c* are along the line 864 in FIG. 20. That is, the bottom surfaces of the array grooves 85*c* extend in a straight line up to point B from one side surface of the second matching layer 88*c* through the interior of the second matching layer 88*c*, similarly to the line 83, but from point B, extend to the side surface of the first matching layer 86*c* opposite the above side surface. Consequently, concerning the first matching layer 86*c*, the depth of the array grooves 85*c* near the above side surface of the first matching layer 86*c* is less than the thickness of the first matching layer 86*c*.

In other portions, the thickness of the array grooves 85*c* is equal to the thickness of the matching layer 86*c*. The first matching layer 86*c* is continuous via the portions 862 of the first matching layer 86*c*, positioned between the bottom surface of the portion of the array grooves 85*c* at which the depth is less than the thickness of the first matching layer 86*c* and the second matching layer 88*c*. The piezoelectric element 84 is divided by the array grooves 85*c*. Each of the divided portions of the piezoelectric element 84 is electrically connected via the portions 862 of the conductive first matching layer 86*c*.

Similarly to the eighth aspect explained using FIG. 18, in an ultrasound transducer array 81*c* configured as explained in detail above, the flexible printed board 94 used as a ground line need be bonded to only a portion of the first matching layer 86*c*, so that a highly reliable ultrasound transducer array 81*c* with simple configuration can be provided.

The ultrasound transducer array 81*c* of this aspect can in essence be manufactured by the first or the second method of manufacture of the ultrasound transducer array 81 of the above-described seventh aspect. However, in the fifth process (the process to form the array grooves), in order to form the array grooves 85*c*, the tip of the blade 93 of the precision cutting machine is for example moved along the line 864 from point A in the direction of the arrow in FIG. 20, stopped at point B, and from point B is removed by moving in the direction perpendicular to the line 864.

Figure 21:
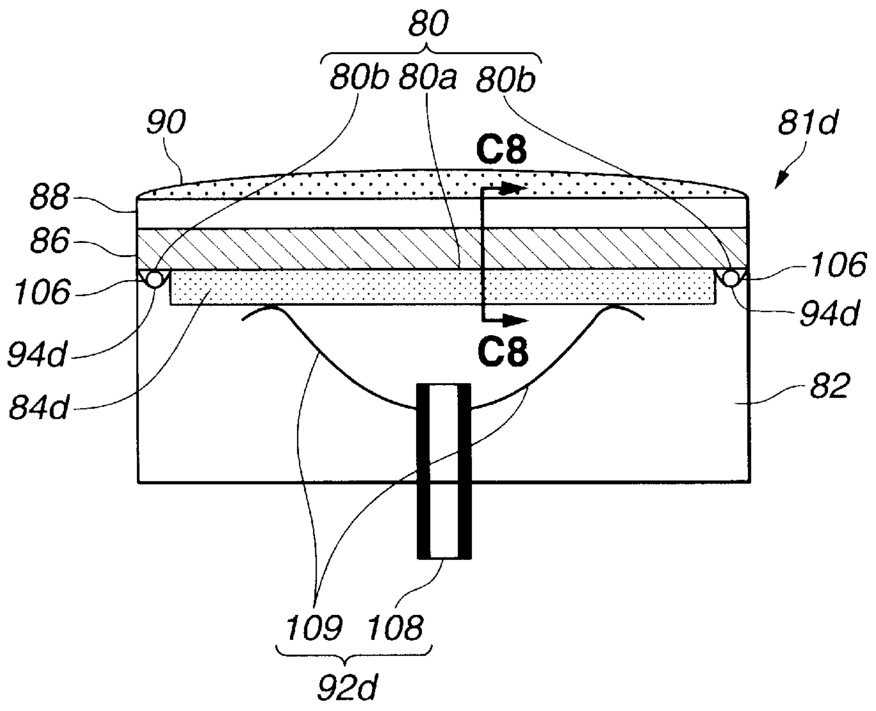
FIG. 21 is a cross-sectional view, showing a section parallel to the front plane, of an ultrasound transducer array of an eleventh aspect of the invention.

An eleventh aspect of this invention is shown in FIG. 21. The figure is a cross-sectional view of the ultrasound transducer array 81*d*, in the plane parallel to the front surface (similar to the surface facing the plane of the paper in FIG. 14).

The configuration of the ultrasound transducer array 81*d* of this aspect is in essence the same as the configuration of the ultrasound transducer array 81 of the seventh aspect. In this aspect, constituent members which are effectively the same as constituent members explained referring to FIG. 14 through FIG. 16 in explaining the seventh aspect are assigned the same reference symbols as those used for the corresponding members of the seventh aspect, and detailed explanations are omitted.

A difference between the configuration of this aspect and the configuration of the seventh aspect is the configuration of the piezoelectric element, signal lines, and ground lines. The lower surface 80 of the first matching layer 86 (the surface opposed to the piezoelectric element 84*d*) is larger than the upper surface of the piezoelectric element 84*d* (the surface opposed to the first matching layer 86). The upper surface of the piezoelectric element 84*d* is an acoustic radiation surface which radiates ultrasound. The lower surface 80 of the first matching layer 86 is used as an opposed region 80. The opposed region 80 comprises the junction region 80*a* joined to the acoustic radiation surface of the piezoelectric element 84*d*, and the regions 80*b* joined to the acoustic radiation surface. Copper wires 94*d* used as ground lines are positioned on the regions 80*b*. The regions 80*b* are used as wiring regions 80*b*. The wires 94*d* are connected to the wiring regions 80*b* using conductive resin 106. The wiring regions 80*b* extend from the front surface of the ultrasound transducer array 81*d* to the back surface (the reverse surface of the front surface) along the side surfaces of the ultrasound transducer array 81*d*, together with the wires 94*d*, and are connected to all the portions of the first matching layer 86 divided by the array grooves 85.

In this aspect, wires 94*d* are shown as one example of conductive members; but the conductive members need not be formed in wire shape, and may instead be formed in ribbon shape, rod shape, or foil shape.

The cross-sectional plane of the layered member along the line C8—C8 is effectively the same as the layered member cross-section shown in FIG. 15. Below the piezoelectric element 84*d*, the substantially flat glass-epoxy resin 108 extends from the front surface of the ultrasound transducer array 81*d* to the back surface (the reverse surface of the front surface) in the direction orthogonal to the direction in which the array grooves 85 extend (the direction perpendicular to the plane of the paper in FIG. 21). A plurality of wires are connected to both ends of the glass-epoxy resin 108. At both ends of the glass-epoxy resin 108, electrodes corresponding to these wires are arranged in the length direction in portions close to the piezoelectric element 84*d*.

These electrodes are connected to the electrodes on the lower surface of portions corresponding to the divided piezoelectric elements 84*d*, via wires 94*d*. The wires 94*d* are connected to the piezoelectric elements 84*d* using solder. The glass-epoxy resin 108 and wires 94*d* are used as signal lines 92*d*. A portion of the glass-epoxy resin 108 and the wires 94*d* are positioned within the back load member 82.

In cases where high-frequency ultrasound is to be used, the first matching layer 86 is made thin. Hence if, as in the seventh aspect, a ground line is connected to a side surface of the first matching layer 86, the area over which the first matching layer 86 is in contact with the ground line (the contact area) is small, and so it is difficult to ensure that conduction faults do not occur.

However, in an ultrasound transducer array 81*d* configured as described in detail above, by connecting a portion of the lower surface of the first matching layer 86 (the surface opposed to the piezoelectric element 84*d*) to the ground line, the contact area is not affected by the thickness of the first matching layer 86, and so conduction faults can be reliably prevented regardless of the frequency of use.

The configuration of the layered member of this aspect is effectively the same as the configuration of the layered member of the seventh aspect shown in FIG. 15, but this invention is not thus limited. For example, the configuration may be effectively the same as the configuration of the eighth aspect shown in FIG. 18, or the ninth aspect shown in FIG. 19. Or, the configuration may be effectively the same as the configuration of the tenth aspect shown in FIG. 20.

Next, the method of manufacture of the ultrasound transducer array 81*d* of this aspect is explained. The ultrasound transducer array 81*d* of this aspect can in essence be manufactured by the first manufacturing method used to manufacture the ultrasound transducer array 81 of the above-described seventh aspect.

First, the layered member is formed according to the first through the third process (process to form the layered member). In the third process, a piezoelectric element 84*d* having an acoustic radiation surface smaller than the lower surface of the first matching layer 86 is prepared. When the piezoelectric element 84*d* is bonded to the first matching layer 86, the piezoelectric element is positioned with respect to the first matching layer 86 such that wiring regions 80*b* are formed.

Next, the array grooves 85 are formed according to the fifth process (process to form array grooves). Then, the wires 94*d* and signal lines 92*d* are connected, and the back load member 82 and acoustic lens 90 are formed.

In cases where high-frequency ultrasound is to be used, as described above, if ground lines are connected to the side faces of the first matching layer 86 as in the seventh aspect, the area over which the first matching layer 86 makes contact with the ground lines (the contact area) is small, and so it is difficult to connect the ground lines to the first matching layer 86.

In this respect, in the method for manufacture of the ultrasound transducer array 81*d* of this aspect, the ground lines are connected to a comparatively large contact area, so that the connection operation is easy. Also, the ground lines can be securely connected, so that manufacturing yields are improved.

Figure 22:
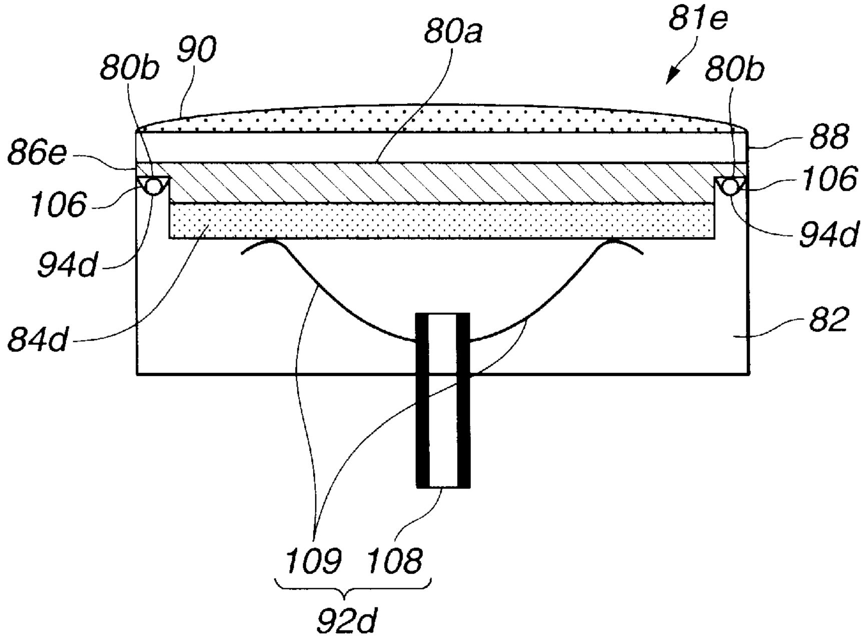
FIG. 22 is a cross-sectional view, showing a section parallel to the front plane, of an ultrasound transducer array of a twelfth aspect of the invention.

FIG. 22 shows a twelfth aspect of the invention. This figure is a cross-sectional view in a plane parallel to the front plane (similar to the plane facing the plane of the paper in FIG. 21) of the ultrasound transducer array 81*e*.

The configuration of the ultrasound transducer array 81*e* of this aspect is in essence the same as that of the ultrasound transducer array 81*d* shown in FIG. 21. A difference in the configuration of this aspect with that of the eleventh aspect is the configuration of the first matching layer.

In the first matching layer 86 shown in FIG. 21 above, the junction region 80*a* and wiring regions 80*b* exist in the same plane. However, in the first matching layer 86*e* of this aspect, the wiring regions 80*b* are sunken with respect to the junction region 80*a*. Even configured in this way, advantageous results similar to those of the ultrasound transducer array 81*d* of the eleventh aspect can be obtained.

Next, a method for manufacturing the ultrasound transducer array 81*e* of this aspect is explained. In essence, manufacture is possible using the second method of manufacture of the ultrasound transducer array 81 of the above-described seventh aspect.

First, the parent layered member shown in FIG. 17 is formed. Then, grooves (hereafter "wiring grooves") are formed along either the vertical lines, or the horizontal lines, of the lines 96 in a lattice shape in the lower surface (the reverse surface of the piezoelectric element 84' that is in contact with the first matching layer 86') of the parent layered member, in order to form the sunken wiring regions 80*b*. The width of the wiring grooves is larger than twice the width of the wiring regions 80*b*. The wiring grooves extend in the depth direction as far as the interior of the first matching layer 86*e*.

Next, the process to cut the parent layered member of the second manufacturing method is performed. However, when cutting along the wiring grooves, cutting is performed through the center in the width direction of the wiring grooves, along the center line extending in the length direction of the wiring grooves. Then, the signal lines 92*d* and wires 94*d* are connected, and the back load member 82 and acoustic lens 90 are formed, similarly to the method for manufacturing the ultrasound transducer array 81*d* shown in FIG. 21.

In the method of manufacture of the ultrasound transducer array 81*d* of the twelfth aspect, when the piezoelectric element 84*d* is bonded to the first matching layer 86, the adhesive may adhere to the wiring regions 80*b*. If so, there is an increased possibility of the occurrence of conduction faults.

With respect to this, in the method of manufacture of the ultrasound transducer array 81*e* of this aspect, by forming the wiring grooves prior to the process of cutting the layered member, adhesive on the wiring regions 80*b* is removed, so that ultrasound transducer arrays 81*e* can be manufactured rapidly and at low cost, and reliability with respect to conduction faults can be improved.

In the eleventh aspect and this aspect, two wires 109, each extending from respective surface of the glass-epoxy resin 108, are used to improve reliability; of course a single wire extending from one surface can also be used to obtain a similar advantageous result.

Figure 23A:
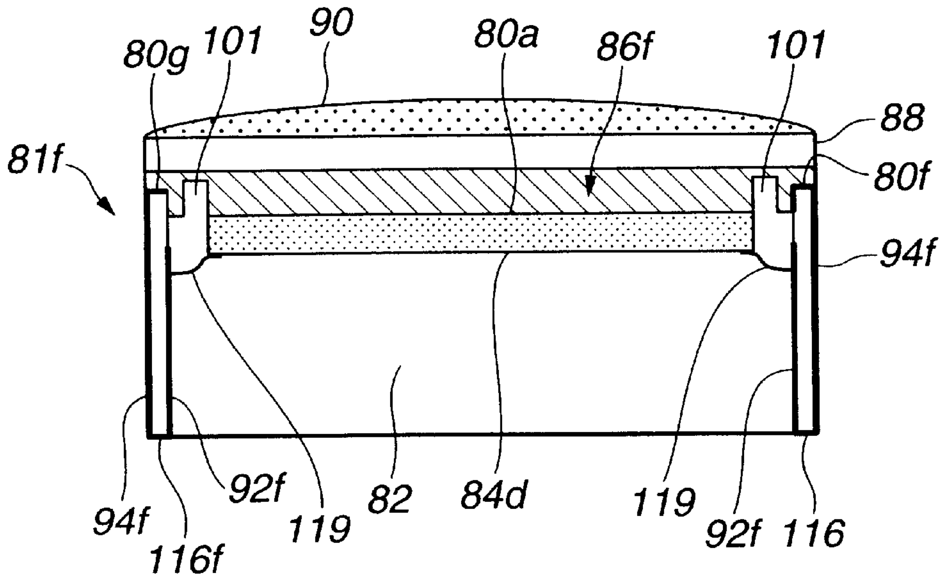
FIG. 23A is a cross-sectional view, showing a section parallel to the front plane, of an ultrasound transducer array.
Figure 23B:
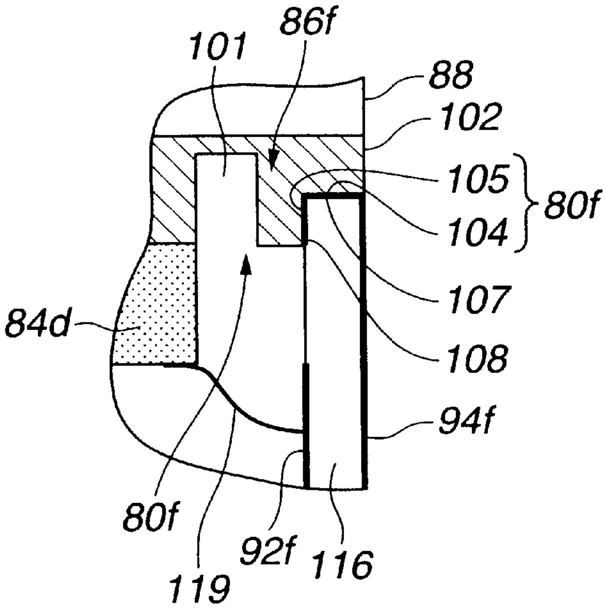
FIG. 23B is an explanatory diagram showing in enlargement the wiring area and groove of the ultrasound transducer array of FIG. 23A.
Figure 24A:
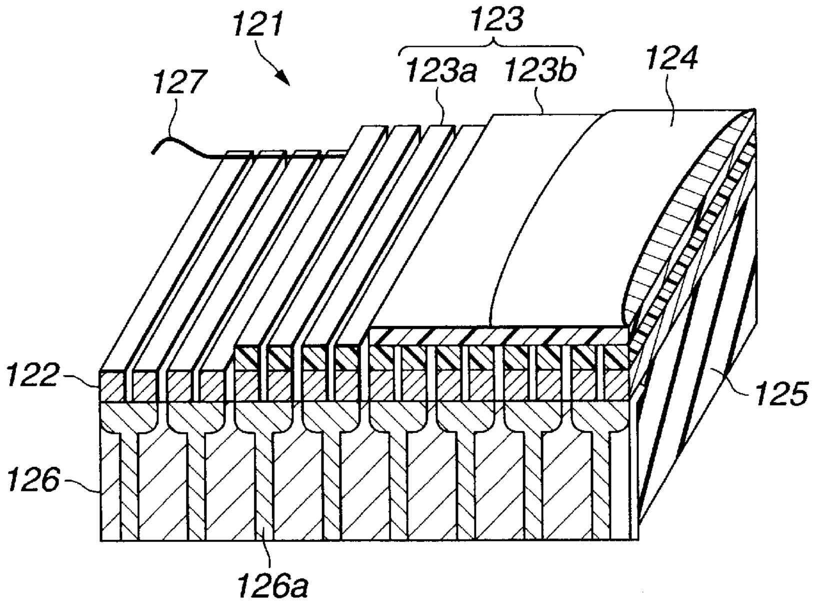
FIG. 24A is a summary perspective view showing the configuration of an ultrasound transducer array.
Figure 24B:
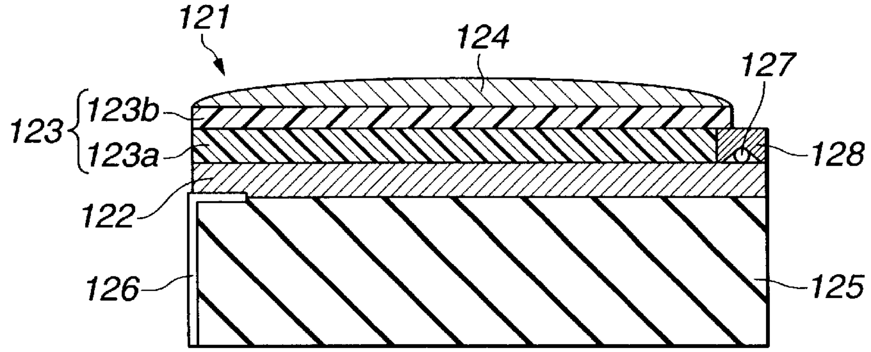
FIG. 24B is a cross-sectional view of FIG. 24A.
Figure 24C:
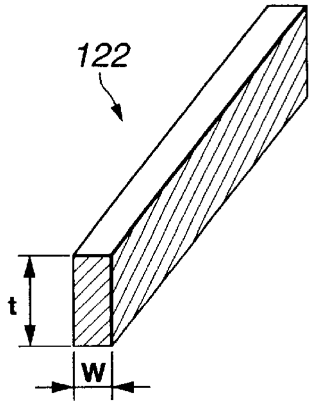
FIG. 24C is a perspective view showing only a piezoelectric element of FIG. 24A.

FIG. 23A and FIG. 23B show a thirteenth aspect of this invention. FIG. 23A is a cross-sectional view of the ultrasound transducer array 81*f* in a plane parallel to the front plane (similar to the plane facing the plane of the paper in FIG. 14); FIG. 23B is an enlarged view of one of the wiring regions 80*f* and one of grooves 101.

Grooves 101 are formed between the junction region 80*a* of the first matching layer 86*f* of this aspect, and the wiring regions 80*f*, 80*g* used for wiring. The configuration of the ultrasound transducer array 81*f* of this aspect is in essence the same as the configuration of the ultrasound transducer array 81*d* shown in FIG. 21.

A difference between the configuration of this aspect and that of the eleventh aspect is the configuration of the matching layer, signal lines and ground lines. The wiring region 80*f* is formed in the portion in contact with the side surface 102 (a side surface adjacent to the front surface). The wiring region 80*f* is defined by the upper surface 104 of the wiring region orthogonal to the side surface 102 which is continuous with the side surface 102 and extends along the side surface 102, and the wiring region side surface 105 which is continuous with the wiring region upper surface 102 and extends parallel to the side surface 102.

A substantially flat glass-epoxy board 116 extends along the side surface (surface adjacent to the front surface) of the ultrasound transducer array 81*f* from the back load member 82 toward the first matching layer 86*f*. One end of the glass-epoxy board 116 is inserted into the wiring region 80*f*.

On the glass-epoxy board 116, a ground electrode is formed in the portion 107 opposed to the wiring region upper surface 104 and in the portion 108 opposed to the wiring region side surface 105, extending along the wiring region 80*f*. That is, the first matching layer 86*f* is in contact on two surfaces with a ground electrode in the wiring region 80*f*. The contact area between the first matching layer 86*f* and the ground electrode is large, so that reliability against electrical conduction faults is high. This electrode is connected to a single wire 94*f* positioned on the surface of the glass-epoxy board 116 facing outside, and is used as a ground line.

The configuration of the wiring region 80*g* and the glass-epoxy board 116*f* which is connected to the wiring region 80*g* is effectively the same as the configuration of the wiring region 80*f* and the glass-epoxy board 116 respectively. A difference between the former and the latter is that an electrode is formed on the portion 108 of the glass-epoxy board 116, but no electrode is formed on the portion of the glass-epoxy board 116*f* corresponding to the portion 108. That is, the first matching layer 86*f* is in contact with a ground electrode at one surface in the wiring region 80*g*.

A plurality of wires 92*f* are positioned as signal lines on the surfaces facing inward of the glass-epoxy boards 116, 116*f*. These wires are connected using solder to the electrodes on the lower surfaces in portions corresponding to divided piezoelectric elements 84*d* via wires 119.

If, as in the conventional ultrasound transducer array 1001 shown in FIG. 30A and FIG. 30B, a ground line 1009 spans two neighboring portions among the plurality of portions of a divided first matching layer 1004, vibrations propagate between these portions via this ground line 1009, so that mechanical cross talk may occur. In this aspect, however, by forming the groove 101, vibrations are not easily transmitted to the glass-epoxy boards 116, 116*f*, so that mechanical cross talk can be prevented.

In this aspect, wires 92*f* used as signal lines are connected using solder to electrodes on the bottom surface of the piezoelectric element 84*d* via wires 119; but this invention is not thus limited. For example, wire bonding may also be used. When using solder, there may be variations in the amount of solder for each of the wires 119, so that differences in loads for different wires 119 may occur. If wire bonding is used, differences in loads can be reduced, and so the characteristics of the ultrasound transducer array 81*f* can be stabilized. Also, solder may be used to make connections via conductors other than wire.

Next, a method of manufacture of the ultrasound transducer array 81*f* of this aspect is explained.

The ultrasound transducer array 81*f* can, in essence, be manufactured by the method of manufacture of the ultrasound transducer array 81*d* of the eleventh aspect shown in FIG. 21.

First, similarly to the eleventh aspect, a layered member having a small piezoelectric element 84*d* is formed. Then, the array grooves 85, wiring regions 80*f*, 80*g*, and grooves 101 are formed. Following this, the glass-epoxy boards 116, 116*f* and wires 119 are mounted, and the back load member 82 and acoustic lens 90 are formed.

In this aspect, a ground electrode to which is connected a wire 94*f* used as a ground line is directly bonded to the first matching layer 86*f* using conductive adhesive; but this invention is not thus limited. For example, wire bonding may be used, similarly to the wires 92*f* used as signal lines. In this case, sputtering or another method is used to provide gold, aluminum, or some other metal on the portion of the first matching layer 86*f* to be wire-bonded. By using wire bonding, the time required for manufacture can be shortened compared with cases in which conductive adhesive is used, so that wire bonding is suited to mass production.

In this aspect, the electrode of the piezoelectric element 84*d* on the side of the first matching layer 86*f* is used as a ground electrode, but if a sufficiently high breakdown voltage is secured for the acoustic lens 90 and second matching layer 88 and similar, the patterning of the glass-epoxy boards 116, 116*f* may be modified, and the signal line and ground line interchanged.

In each of the aspects described above, a piezoelectric ceramic obtained by ordinary sintering is used as the piezoelectric element; but a piezoelectric single crystal may be used instead.

In each of the above-described aspects, the ultrasound transducer arrays 81 and 81*a* to 81*e* have been described in detail as having divided piezoelectric element portions arranged in a one-dimensional array. Of course, a carbon composite material containing carbides, of which material itself has small ultrasound attenuation and an optimal acoustic impedance, is easily machined and can be formed into thin shapes, can be applied to an ultrasound transducer array using a piezoelectric element not divided by array grooves or to an ultrasound transducer array in which divided piezoelectric element portions are arranged in two dimensions.

Below, the dimensions of elements in the configuration of the ultrasound transducer arrays described thus far are explained.

Figure 31:
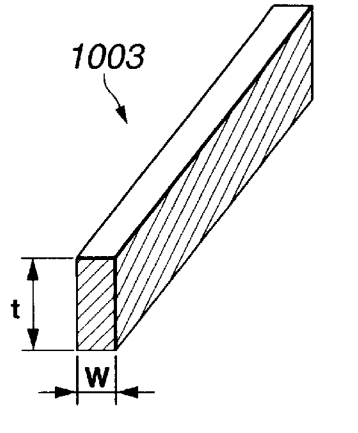
FIG. 31 is a perspective view showing only a piezoelectric element of FIG. 30A.

In Japanese Patent Publication No.62-2813, for example, an embodiment is proposed in which an ultrasound transducer array 1001 has a ratio w/t of the width w in the array direction of a single piezoelectric element 1003, shown in FIG. 31, to the thickness t in the acoustic radiation axis direction, being equal or less than 0.8, and in particular being w/t=0.66 (w=0.4 mm, t=0.6 mm).

However, if in the ultrasound transducer array of the above Japanese Patent Publication No.62-2813 the ratio w/t of the width in the array direction of a single piezoelectric element 1003 to the thickness t in the acoustic radiation axis direction of the above piezoelectric element 1003 is made much smaller than 0.8, the problem described below occurs.

If the ratio w/t of the width w to the thickness t of the above piezoelectric element 1003 is set such that w/t<0.3, vibration modes in the transverse direction are small, but higher-order vibrations in the thickness direction become large. In an ultrasound transducer array 1001 configured with at least one row of such piezoelectric elements 1003, high-harmonic vibrations will occur (see FIG. 25A, FIG. 25B).

Due to this occurrence of high harmonics, energy in the ultrasound transducer array 1001 is also distributed to high harmonic components, so that there is energy loss in the fundamental frequency component, and the sensitivity declines.

Also, because of the presence of these high harmonic components in the ultrasound transducer array 1001, disorder appears in the transmitted sound field formed by electronic focusing in order to electronically focus the ultrasound, so that artifacts occur, and the accuracy of the result of ultrasound beam synthesis upon reception is reduced. Consequently the resolution of the resulting ultrasound diagnostic image is degraded.

On the other hand, if the ratio w/t of the width w to the thickness t of the above piezoelectric elements 1003 is set to 0.6 to 0.8, the electromechanical transduction efficiency is improved, but transverse-direction vibration modes appear. Consequently problems similar to the above-described high harmonic components arise, cross talk and increases in pulse width occur due to radial-direction vibrations, and there is degradation of the resolution of ultrasound diagnostic images resulting from imaging.

Hence the piezoelectric element 1003 must have a high electromechanical transduction efficiency and must be of a shape which suppresses the occurrence of unnecessary vibration modes.

Therefore, the provision of an ultrasound transducer array having piezoelectric elements with a high electromechanical transduction efficiency, of an optimal shape for suppressing the occurrence of unnecessary vibration modes, and enabling the enhancement of image resolution, is desired.

Below, fourteenth through sixteenth aspects of this invention are explained, referring to FIG. 24 through FIG. 29.

FIG. 24 through FIG. 27 show a fourteenth aspect of this invention. As shown in FIG. 24A through FIG. 24C, the ultrasound transducer array 121 of this aspect comprises a plurality of piezoelectric elements 122 which generate ultrasound and which transmit and receive this ultrasound; a piezoelectric element, positioned on the acoustic radiation surface side of the above plurality of piezoelectric elements 122, which radiates the ultrasound generated by the above plurality of piezoelectric elements 122; an acoustic lens 124, positioned further on the acoustic radiation surface side than the above piezoelectric element 123; and a backing member 125, positioned on the back side of the above plurality of piezoelectric elements 122, as a back load member to absorb unnecessary ultrasound. In this ultrasound transducer array 121, the above plurality of piezoelectric elements 122 are configured to form at least a one-dimensional array.

The above piezoelectric elements 122 are formed from, for example, soft lead zirconate titanate, $Pb(Zr,Ti)O_3$, or other PZT-system piezoelectric ceramic material, with electrodes formed on both surfaces. The above acoustic lens 124 is formed from silicone resin. The above piezoelectric element 123 is configured from, for example, a first piezoelectric element 123*a* formed from an epoxy resin with alumina as a filler on the acoustic radiation surface side of the piezoelectric elements 122, and a second piezoelectric element 123*b* formed from an uncombined epoxy resin, further on the acoustic radiation surface side further than the first piezoelectric element 123*a*.

The above backing member 125 is formed from urethane with alumina as a filler. The above piezoelectric elements 122 are connected on the signal line side by a flexible printed board 126 on which a pattern 126*a* is formed; the grounds on the sides of the above first and second piezoelectric elements 123*a*, 123*b* are connected by solder or conductive adhesive using a ground line 127 as a common connection, and covered by a protective resin 128. As the ground line 127, a conductive wire or foil is used.

The 3 MHz ultrasound transducer array 121 of this aspect is manufactured by the following method.

First, a 250 μm thin sheet for the first piezoelectric element 123*a* (with acoustic impedance approximately 7.5 MRayl) is ground. Then, one surface of the first piezoelectric element 123*a* is masked with tape or similar, and the second piezoelectric element 123*b* is formed to a thickness of 190 μm on the unmasked surface.

Next, a piezoelectric element 122 approximately 500 μm thick is fixed with adhesive to the above first piezoelectric element 123*a*, and a flexible printed board 126 is joined with solder to the above piezoelectric elements 122.

Following this, backing material 125 is poured onto and joined with the back side of the above plurality of piezoelectric elements 122, and wax is used to fix the assembly onto a base, or tape is used to fix it in place. In this state, cutting is performed from the side of the above piezoelectric elements 122, to form the ultrasound transducer array.

In performing cutting, a precision cutting machine is employed, using a 60 μm thick blade, and cutting at a pitch of 0.3 mm. At this time, the ratio w/t of the width in the array direction of the above piezoelectric elements 122 to the thickness t of a single piezoelectric element 122 in the acoustic radiation axis direction is w/t=0.48.

After cutting, lead wires and solder are used for joining to the surface electrodes on the piezoelectric element 123 side of the piezoelectric elements 122 to make a common GND electrode. Finally, the acoustic lens 124 is formed from silicone resin, to obtain the transducer.

Figure 25A:
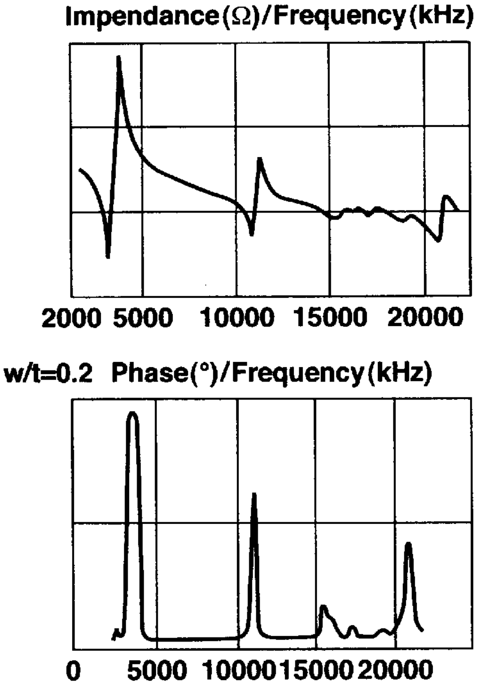
FIG. 25A is a graph showing the impedance curve when w/t =0.2.
Figure 25B:
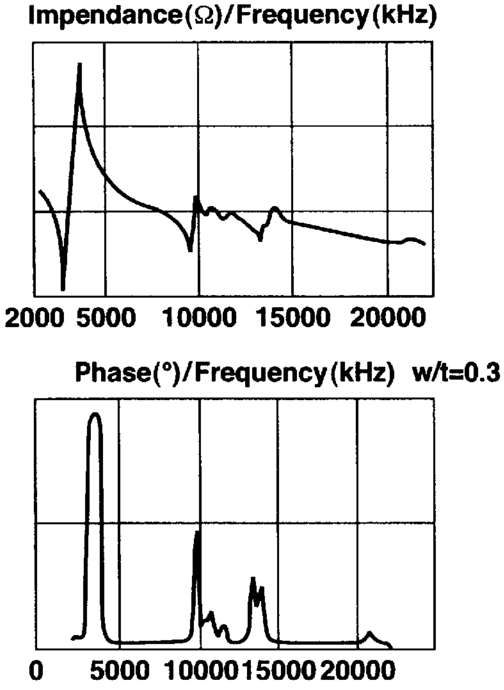
FIG. 25B is a graph showing the impedance curve when w/t =0.3.
Figure 25C:
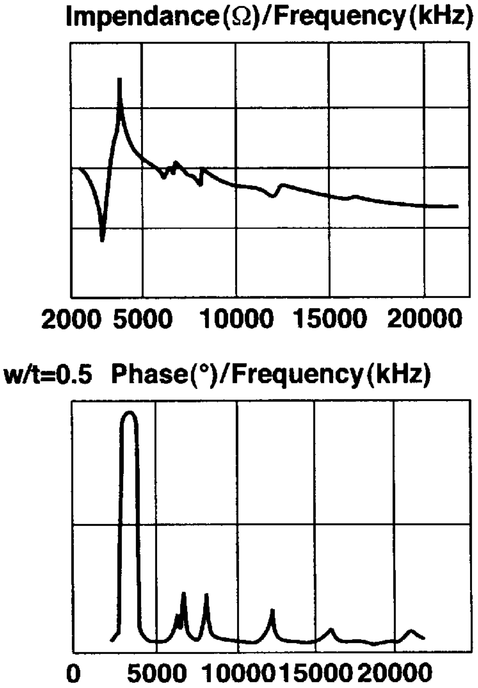
FIG. 25C is a graph showing the impedance curve when w/t =0.5.
Figure 25D:
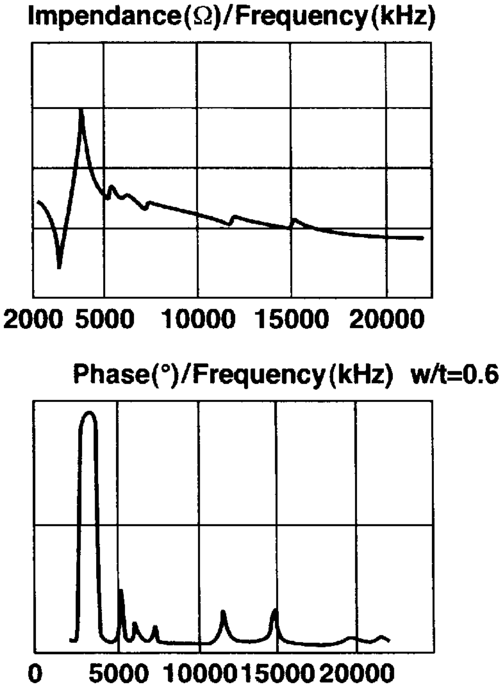
FIG. 25D is a graph showing the impedance curve when w/t =0.6.
Figure 26A:
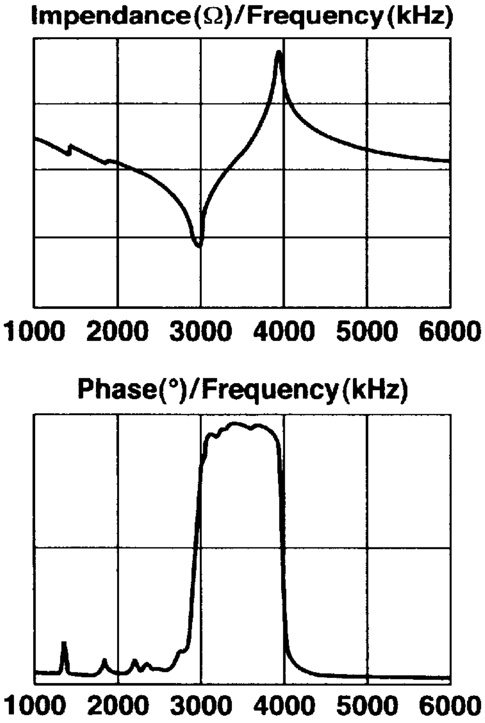
FIG. 26A is a graph showing the impedance curve near the fundamental resonance point when w/t=0.5.
Figure 26B:
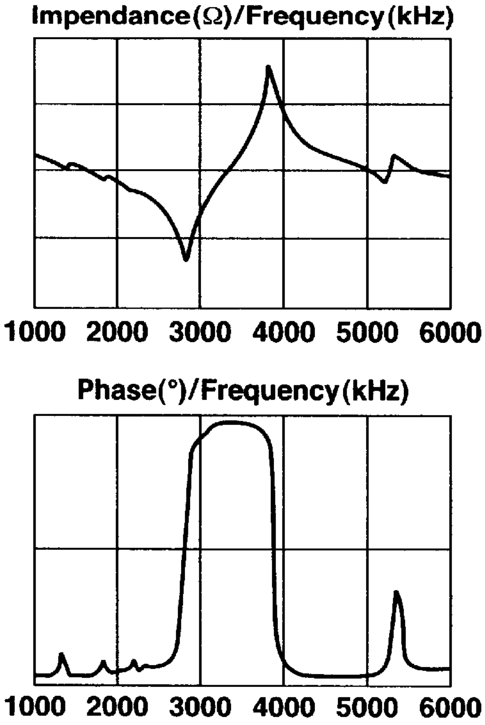
FIG. 26B is a graph showing the impedance curve near the fundamental resonance point when w/t=0.6.
Figure 26C:
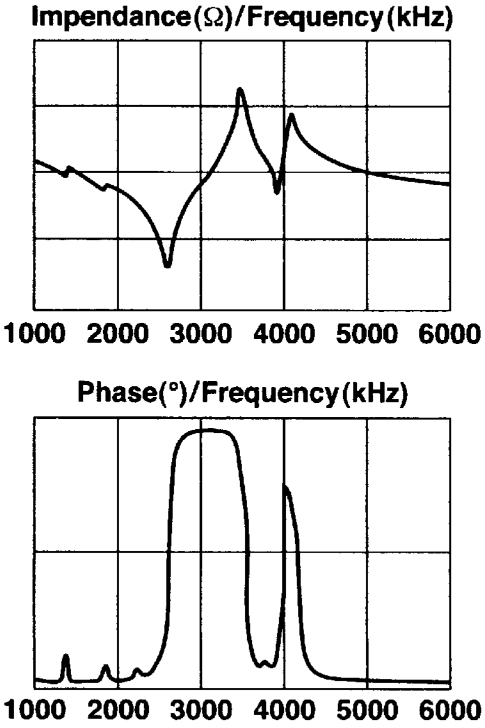
FIG. 26C is a graph showing the impedance curve near the fundamental resonance point when w/t=0.8.

Upon varying the ratio w/t of the width w in the array direction of the piezoelectric elements 122 to the thickness t of the above piezoelectric elements 122 in the acoustic radiation axis direction, impedance curve such as those shown in FIG. 25A to FIG. 25D, and in FIG. 26A to FIG. 26C, are obtained.

FIG. 25A to FIG. 25D, and FIG. 26A to FIG. 26C, are graphs showing the impedance curve (acoustic impedance and phase versus frequency) when the ratio w/t of the width w to the thickness t of the piezoelectric elements 122 is varied.

Here, FIG. 25A is a graph showing the impedance curve when w/t=0.2; FIG. 25B is a graph showing the impedance curve when w/t=0.3; FIG. 25C is a graph showing the impedance curve when w/t=0.5; and FIG. 25D is a graph showing the impedance curve when w/t=0.6. Further, FIG. 26A is a graph showing the vicinity of the fundamental resonance for w/t=0.5; FIG. 26B is a graph showing the vicinity of the fundamental resonance for w/t=0.6; and FIG. 26C is a graph showing the vicinity of the fundamental resonance for w/t=0.8.

The phase is the phase difference between the current and the voltage of the driving signal driving the piezoelectric elements 122. The magnitude of the acoustic impedance is minimum at the point where this phase difference is zero, at which all the electrical energy supplied to the piezoelectric elements 122 is being converted into vibrational energy.

When w/t<0.3, transverse-direction vibration modes are small, but thickness-direction higher-order vibrations are increased. More specifically, at w/t=0.2 third- and higher-order harmonics are larger, and as w/t is increased, higher-order mode vibrations diminish.

On the other hand, when w/t>0.6, a vibration component occurs in lateral directions perpendicular to the polarization axis of the piezoelectric elements 122. Consequently when an ultrasound transducer array 121 is configured using piezoelectric elements 122 with w/t>0.6, unwanted vibration modes appear. Hence a problem similar to the above-described harmonic components arises, and cross talk and pulse widths are increased, so that image accuracy is worsened during imaging.

FIG. 27A through FIG. 27D show graphs of the echo waveforms and spectrums of ultrasound transducer arrays 121 similarly fabricated using 5 MHz piezoelectric elements 122, with the ratio w/t of the width w to the thickness t of the piezoelectric elements 122 varied, and measured using a flat stainless steel reflecting sheet.

Figure 27A:
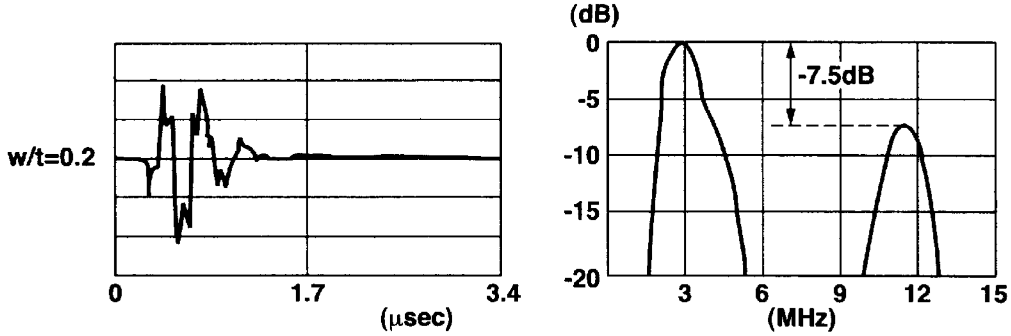
FIG. 27A is a graph showing the echo waveform and spectrum of an ultrasound transducer array for which w/t=0.2.
Figure 27B:
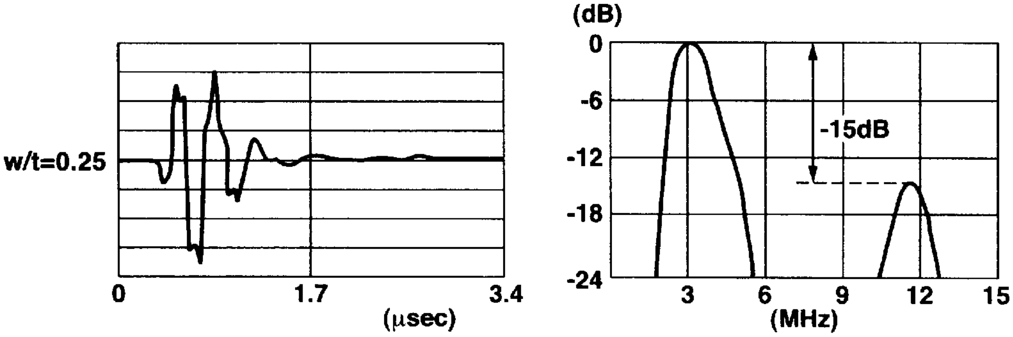
FIG. 27B is a graph showing the echo waveform and spectrum of an ultrasound transducer array for which w/t=0.25.
Figure 27C:
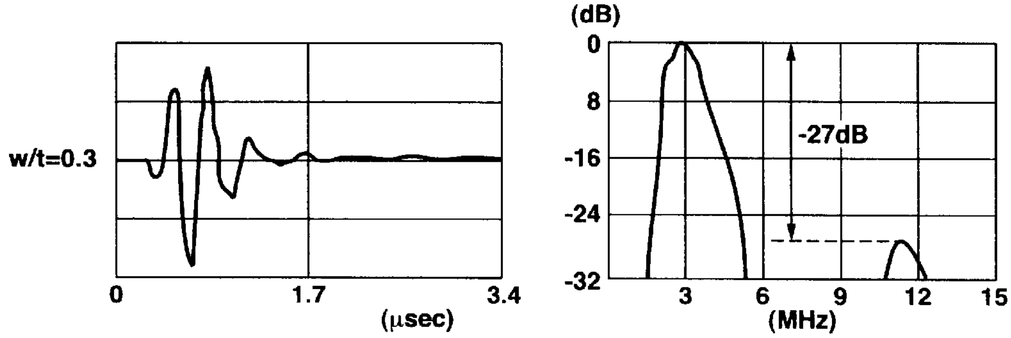
FIG. 27C is a graph showing the echo waveform and spectrum of an ultrasound transducer array for which w/t=0.3.

Here, FIG. 27A shows the echo waveform and spectrum for w/t=0.2; FIG. 27B shows the echo waveform and spectrum for w/t=0.25; FIG. 27C shows the echo waveform and spectrum for w/t=0.3; and FIG. 27D shows the echo waveform and spectrum for w/t=0.5.

For example, when w/t<0.25 as shown in FIG. 27A and FIG. 27B, large harmonic components appear in the echo waveform, and the waveform is disturbed. It is difficult to completely eliminate these harmonic components even when using a bandpass filter.

Figure 27D:
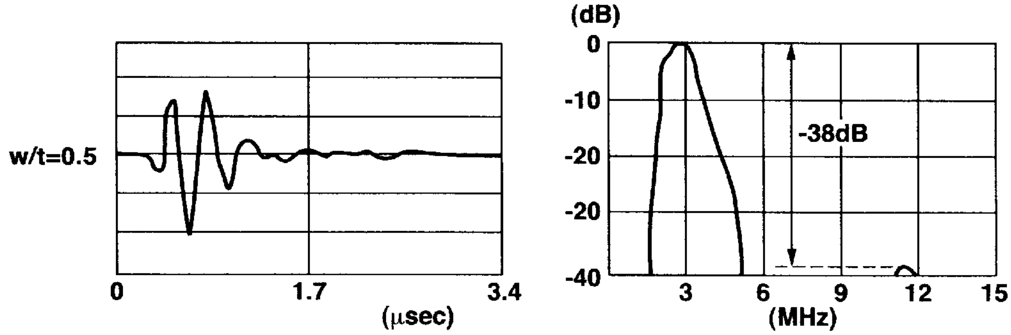
FIG. 27D is a graph showing the echo waveform and spectrum of an ultrasound transducer array for which w/t=0.5.

On the other hand, as shown in FIG. 27C and FIG. 27D, when w/t=0.3 and w/t=0.5, the harmonic components appearing in the echo waveform are extremely small, and there is no disturbance of the waveform.

From these results it is found that in order to efficiently vibrate the piezoelectric elements 122 and suppress higher-order modes and transverse-direction vibrations, the ratio w/t of the width w in the array direction of the piezoelectric elements 122 to the thickness t of the above piezoelectric elements 122 in the acoustic radiation axis direction must be set within $0.3 \leq w/t \leq 0.5$.

In this aspect, the ratio w/t of the width w of piezoelectric elements 122 in the array direction to the thickness t of the above piezoelectric elements in the acoustic radiation axis direction is set to 0.3 to 0.5, and, in the case of soft PZT-system materials, preferably to w/t=0.4 to 0.5 in order to more effectively suppress higher-order vibration modes.

By setting the w/t ratio of piezoelectric elements 122 to 0.3 to 0.5, and preferably to an optimal value of 0.4 to 0.5, higher-order vibration modes, transverse-direction vibration modes, and other unwanted vibration modes are suppressed, only a simple filter is necessary for imaging, energy losses are reduced, and high-sensitivity piezoelectric elements 122 can be realized inexpensively.

In this aspect, an ultrasound transducer array 121 arranged linearly was described; however, the plurality of piezoelectric elements 122 may be curved in a divided manner, to apply this invention to a convex-type ultrasound transducer array.

Figure 28:
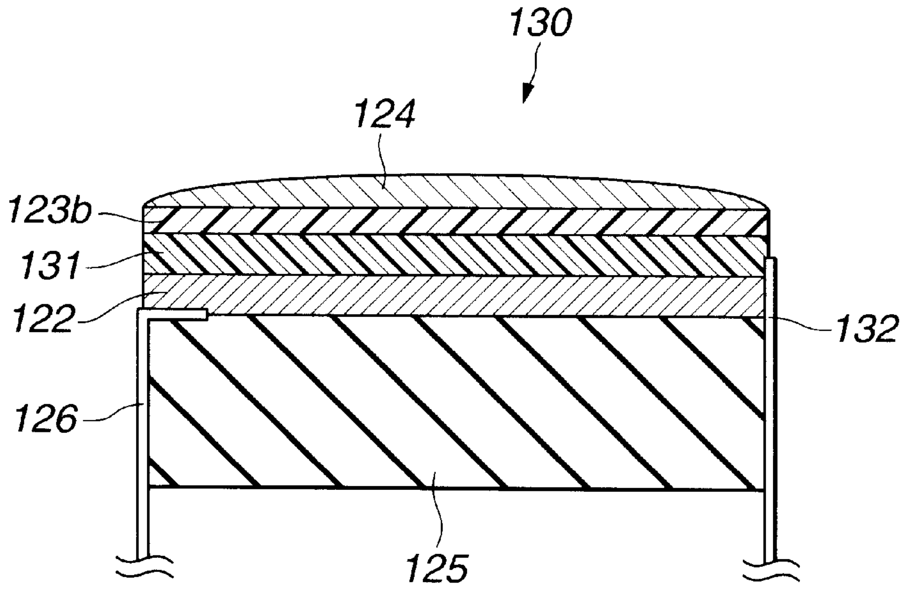
FIG. 28 is a summary cross-sectional view showing an ultrasound transducer array of a fifteenth aspect of the invention.

FIG. 28 shows a fifteenth aspect of this invention.

In the above-described fourteenth aspect, an ultrasound transducer array 121 is configured by forming a first piezoelectric element 123*a* from epoxy resin using alumina as a filler; in this aspect, the first piezoelectric element 123*a* is formed from carbon to configure the ultrasound transducer array 121. Otherwise the configuration is substantially the same as that of the above fourteenth aspect, and an explanation is omitted; similar constituent components are assigned the same symbols in the explanation.

As shown in FIG. 28, the ultrasound transducer array 130 of this aspect is configured having a first matching layer 131 formed from a carbon composite containing ultra-fine particles of silicon carbide (SiC) and boron carbide ($B_4C$) on the acoustic radiation surface side of the piezoelectric element 122.

The 5 MHz ultrasound transducer array of this invention is manufactured by the following method.

First, the carbon composite material which is to become the first matching layer 131, prepared containing ultra-fine particles of silicon carbide (SiC) and boron carbide ($B_4C$), is ground to a thickness of 200 μm. Here the carbon composite material is graphite (carbon) containing fine particles of SiC and $B_4C$. This carbon composite material has wedge-shape fine ceramic particles intermixed between grains of the above graphite (carbon) to suppress the growth of microcracks and greatly increase strength compared with graphite. Consequently, even when machined to a thin shape (under 100 μm) for use at still higher frequencies of 10 MHz or higher, this carbon composite material can be machined comparatively easily by using a two-sided lapping machine and using wax, water-soluble adhesive or similar to affix the material to a base for grinding and polishing.

The carbon composite material used in this aspect contains SiC with an average grain diameter 0.5 μm at a mass fraction of 6 wt %, $B_4C$ with an average grain diameter of 5 μm at a mass fraction of 9 wt %, and 4 wt % zirconium boride. The acoustic impedance of this carbon composite material is approximately 8.5 MRayl.

Next, one side of the first matching layer 131 formed from this carbon composite material is masked with tape or similar, and a resin layer 100 μm thick is formed from epoxy resin on the unmasked side to form the second piezoelectric element 123*b*. Then, a piezoelectric element 122, approximately 300 μm thick, is fixed with adhesive to the above first matching layer 131, and a flexible printed board 126 provided with a pattern is joined with solder to the piezoelectric element 122.

Thereafter, wax is used to fix to a base, or tape is used to fix in place, the layered member. In this state, cutting is performed from the side of the above piezoelectric element 122 to midway through the second piezoelectric element 123*b*, to form the ultrasound transducer array.

In this cutting, a precision cutting machine is used, employing a 30 μm thick blade, cutting at a pitch of 130 μm. At this time, the ratio w/t of the width w in the array direction of one piezoelectric element 122 to the thickness t of the piezoelectric element 122 in the acoustic radiation axis direction is w/t=0.33. The ultrasound transducer array of this aspect has a so-called sub-diced configuration, in which two elements are connected in a single pattern.

Next, after a backing material 125 formed from epoxy resin with an alumina filler, used as a back load member, is poured onto and joined with the reverse side of the piezoelectric element 122, the side surfaces of the above first matching layer 131 are cleaned.

Then, a flexible printed board 132 having a full-coverage electrode is joined to the surface electrode on the side of the piezoelectric element 123 of the piezoelectric element 122 using conductive adhesive, for use as a common GND electrode. Finally, an acoustic lens 124 is formed from silicone resin, to complete fabrication of the transducer.

Similarly to the above-described fourteenth aspect, if the configuration of the transducer of this ultrasound transducer array 130 configured in this way is varied, including the first and second matching layer 131, 123*b*, the third- and higher-order harmonics are increased for w/t=0.25 or less, and as the w/t ratio is increased, higher-order vibration modes diminish.

If the fabricated ultrasound transducer array 130 has a w/t ratio of 0.25 or less, large harmonic components appear in the echo waveform and cannot easily be eliminated completely even using a band-pass filter.

As shown in FIG. 25A through FIG. 25D and FIG. 26A through FIG. 26C, when the w/t ratio is 0.6 or higher, vibration components in transverse directions perpendicular to the polarization axis appear, so that when used in an ultrasound transducer array 121, unwanted vibration modes are present. Consequently a problem similar to that of the above-mentioned high harmonic components arises, and there are increases in cross talk and in pulse widths, so that the image accuracy upon imaging is degraded.

As a result, similarly to the above-described fourteenth aspect, in order that the piezoelectric element 122 vibrates efficiently, and in order to suppress higher-order modes and transverse-direction vibrations, the ratio w/t of the width w of the piezoelectric element 122 in the array direction to the thickness t of the above piezoelectric element 122 in the acoustic radiation axis direction must be set in the range $0.3 \leq w/t \leq 0.5$.

In this aspect, similarly to the above-described fourteenth aspect, the ratio w/t of the width w of piezoelectric elements 122 in the array direction to the thickness t of the above piezoelectric elements in the acoustic radiation axis direction is set to 0.3 to 0.5, and, in the case of soft PZT-system materials, preferably to w/t=0.4 to 0.5 in order to more effectively suppress higher-order vibration modes.

By this means, advantageous results similar to those of the ultrasound transducer array 121 of the above-described fourteenth aspect can be obtained from the ultrasound transducer array 130 of this aspect.

Because the first matching layer 131 formed from the above carbon composite material is conductive, in addition to functioning as a matching layer, it can also be used as an electrode from the piezoelectric element 122.

In this aspect, the piezoelectric element 122 and the first matching layer 131 are electrically connected via a thin adhesive layer, and by connecting wires to this first matching layer 131, a common electrode for the piezoelectric elements 122 after cutting is formed. Also, the exposed side-surface electrode of the piezoelectric element 122 has more area available for wiring than the side surface of the above first matching layer 131, so that wiring reliability is improved. Further, in a configuration in which wiring is performed from the side surface of the first matching layer 131, the acoustic radiation area can be made large with respect to the size of the transducer, so that the device size can be easily reduced.

Though not shown in FIG. 28, the signal electrode side of the piezoelectric element 122 and the flexible printed board 132 which serves as the common GND electrode must be insulated. As the method of insulation, a method is used in which a polyimide insulator is positioned in the portion neighboring the piezoelectric element 122 of the flexible printed board 132 itself. Other possible insulation methods are available not by providing a full-surface electrode on the piezoelectric element 122 but by providing a portion without an electrode in the region neighboring the flexible printed board 132, or by sealing the exposed signal electrode of the piezoelectric element 122 with resin or similar means.

Figure 29:
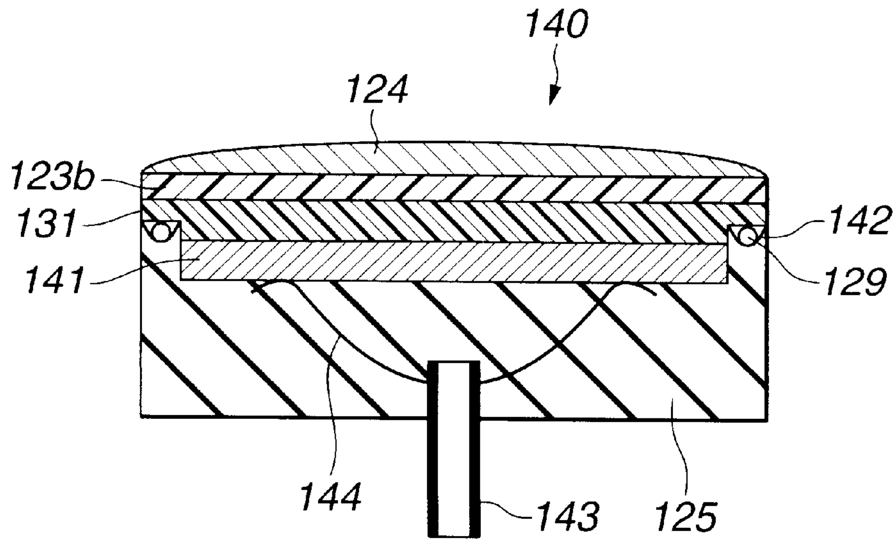
FIG. 29 is a summary cross-sectional view showing an ultrasound transducer array of a sixteenth aspect of the invention.

FIG. 29 shows the ultrasound transducer array of a sixteenth aspect of the invention. This aspect is a modification of FIG. 28; in the ultrasound transducer array 140 shown in the figure, first and second matching layers 131, **123*b* are layered as shown in FIG. 28, and are joined to a piezoelectric element 141 which is somewhat smaller than these first and second matching layers 131, 123*b***.

Then, wax is used to fix to a base, or tape is used to fix in place, the layered member. In this state, cutting is performed from the side of the above piezoelectric element 141 to midway through the second piezoelectric element **123*b***, to form the ultrasound transducer array in which the w/t ratio is 0.3 to 0.5, and preferably an optimal value of 0.4 to 0.5.

After cutting, the divided first matching layer 131 is connected using copper wires 129 and conductive resin 142, and the signal-line is connected by solder to each piezoelectric element 141 using fine wires 144 from substantially the distal end of the glass-epoxy board 143 with patterns formed on both sides.

A framework, not shown, is provided on both ends of the above first matching layer 131, and a groove portion formed is filled with backing material 125 to form the back load member, and in addition the acoustic lens 124 is formed from silicone resin to fabricate the transducer.

Advantageous results similar to those of the above-described fourteenth and fifteenth aspects are obtained from the ultrasound transducer array 140 configured in this way, and in cases where wiring is difficult from the side surface of the first matching layer 131, which is made thin for operation at higher frequencies, wiring operations are made easy, and manufacturing yields are improved.

In this variant, the first and second matching layers 131, **123*b* are layered, and are joined to a piezoelectric element 141 somewhat smaller than these first and second matching layers 131, 123*b* to form a layered member, after which, by cutting to a depth such that a portion of the cut reaches the first matching layer 131, a region for ground wiring is formed. Then, dicing is performed to form the array elements, and by connecting wires 129 using conductive resin 142 a common electrode is formed, to fabricate the ultrasound transducer array 140**. After bonding, wiring is performed in portions at the cut in the carbon material, so that there are no conduction faults due to adhesive, and manufacturing yields and reliability are improved.

In this aspect, the first matching layer 131 is cut completely through; however, by leaving a slight amount in the depth direction, or by providing a remaining portion at an edge, there is no need to connect a common ground to each piezoelectric element after cutting, so that an array can be fabricated inexpensively and with high reliability. Further, by cutting through 80% or more of the piezoelectric element 141 in the depth direction, piezoelectric elements 141 can be fabricated with a high electromechanical transduction efficiency, regardless of the presence of the first matching layer 131.

Because after cutting the neighboring piezoelectric elements 141 are connected, the problem of cross talk arises. However, by leaving material on the common GND electrode side, the need for wiring is eliminated, and the transducer can be manufactured inexpensively. And by cutting into only the sub-diced portion to midway through the piezoelectric element 141, or to midway through the first matching layer 131, which is a conductive matching layer, cross talk can be suppressed and wiring reliability improved.

Similarly to the fourteenth aspect, by curving the array in a state in which a plurality of piezoelectric elements 141 are separated, a convex-shape ultrasound transducer array can be manufactured.

Various variants of each of the configurations of the above-described fourteenth through sixteenth aspects are conceivable; representative examples of these are indicated below.

In addition to PZT-system piezoelectric ceramics and other PMN-system piezoelectric ceramics obtained by ordinary sintering, similar advantageous results can be obtained by using materials such as piezoelectric single crystals as the piezoelectric element 141.

The method of manufacture of transducers is not limited to only those of the above-described aspects; for example, a second piezoelectric element **123*b* using epoxy resin may be ground and shaped to a prescribed thickness, a first piezoelectric element 123*a* formed by pouring an epoxy resin with alumina filler, then grinding and shaping, and after fixing in place the piezoelectric element 141 using an adhesive, dicing is performed from the side of the piezoelectric element 141 to midway through the second piezoelectric element 123*b***, such that the w/t ratio is from 0.3 to 0.5.

Compared with such a backing member 125 as a back load member, by forming a hard piezoelectric element 123 and then cutting from the side of the piezoelectric element 141, the precision in the depth direction is improved, there is little vibration in the piezoelectric element 141 during cutting, chipping and other problems tend not to occur, and groove widths are stable. Consequently the width of the piezoelectric elements 141 can be reduced for use at high frequencies, and sizes can be reduced, to manufacture transducers with good yields.

As explained using FIG. 29, a framework, not shown, is provided after wiring signal-side, and an epoxy resin, which remains flexible after hardening, intermixed with alumina, zirconia or similar insulating powder is poured into the framework to form the backing member 125 as a back load member; by this means, an adhesive layer is not necessary, scattering in reflections at interfaces is small, and stable transducers can be formed. Of course each of the configurations of the aspects here described can be variously modified and altered.

This invention is not limited only to the above aspects; if the width w in the array direction of the above piezoelectric element 141 is the width w perpendicular to the acoustic radiation axis of the above piezoelectric element 141, an ultrasound transducer array 140 may also be configured in which the ratio of the width w perpendicular to the acoustic radiation axis of the above piezoelectric element 141 to the thickness t of the above piezoelectric element 141 in the acoustic radiation axis direction is from 0.3 to 0.5, and more preferably from 0.4 to 0.5.

Having described the preferred embodiments of the invention referring to the accompanying drawings, it should be understood that the present invention is not limited to those precise embodiments, and that various changes and modifications thereof could be made by one skilled in the art without departing from the spirit or scope of the invention as defined in the appended claims.

As explained above, in this invention divided grooves are formed to a depth such that piezoelectric elements are separated, reaching the matching layer, and the thickness of remaining material in the matching layer is made small, such that cross talk can be sufficiently suppressed, and filler material can be used to prevent a reduction in the strength.

What is claimed is:

1. An ultrasound transducer array, in which a plurality of piezoelectric elements, which can be electrically operated independently, are arranged in an array, and comprising:

one or a plurality of matching layers, provided on the acoustic radiation surface side of said piezoelectric elements;

a conductive material layer, provided on the side of said matching layer joined with said piezoelectric elements, in the direction along the array direction, a portion of which is in contact with and electrically connected to said piezoelectric elements along said array direction, and a portion of which is not in contact with said piezoelectric elements along said array direction;

a plurality of grooves, which mechanically and electrically insulate said piezoelectric elements and at least a portion of said matching layer for each electrically independently operable element; and, conductive material, which fills at least a part of the portions of said grooves formed where said piezoelectric elements and said conductive material layer are not in contact.

2. The ultrasound transducer array according to claim 1, wherein said conductive material layer is formed from a first thermosetting base resin, and said conductive material used for filling is formed from a second thermosetting base resin.

3. The ultrasound transducer array according to claim 2, wherein said first thermosetting base resin and said second thermosetting base resin are the same.

4. The ultrasound transducer array according to claim 2, wherein, of said matching layer, the layer adjacent to said piezoelectric elements is formed from a carbon composite material containing carbides.

5. The ultrasound transducer array according to claim 4, wherein said conductive material layer and said filler conductive material are formed from a thermosetting resin intermixed with carbon powder.

6. The ultrasound transducer array according to claim 5, wherein said carbon powder is a powder of the carbon composite material of said matching layer.

7. The ultrasound transducer array according to claim 2, having a conductive member which makes a common electrical connection to said plurality of electrically independently operable piezoelectric elements along said array direction, and wherein said conductive member is fixed to said conductive material layer by said filled conductive material.

8. The ultrasound transducer array according to claim 2, wherein the ratio of the width w in the array direction to the thickness t in the ultrasound radiation direction of said plurality of piezoelectric elements is from 0.3 to 0.5.

9. The ultrasound transducer array according to claim 8, wherein the ratio of the width w in the array direction to the thickness t in the ultrasound radiation direction of said plurality of piezoelectric elements is from 0.4 to 0.5.

10. The ultrasound transducer array according to claim 1, wherein, of said matching layers, the layer adjacent to said plurality of piezoelectric elements is formed from a carbon composite material containing carbides, and also serves as said conductive material layer.

11. The ultrasound transducer array according to claim 10, wherein said filled conductive material is formed from a thermosetting resin base intermixed with carbon powder.

12. The ultrasound transducer array according to claim 10, wherein said carbon composite material containing carbides contains, as said carbides, fine powder of silicon carbide or of boron carbide.

13. The ultrasound transducer array according to claim 10, wherein said carbon composite material containing carbides contains silicon carbide as said carbides, and also contains a fine powder of borides.

14. The ultrasound transducer array according to claim 10, having a conductive member which makes a common electrical connection to said plurality of electrically independently operable piezoelectric elements along said array direction, and wherein said conductive member is fixed to said conductive material layer by said filled conductive material.

15. The ultrasound transducer array according to claim 10, wherein the ratio of the width w in the array direction to the thickness t in the ultrasound radiation direction of said plurality of piezoelectric elements is from 0.3 to 0.5.

16. The ultrasound transducer array according to claim 15, wherein the ratio of the width w in the array direction to the thickness t in the ultrasound radiation direction of said plurality of piezoelectric elements is from 0.4 to 0.5.

17. The ultrasound transducer array according to claim 1, having a conductive member which makes a common electrical connection to said plurality of electrically independently operable piezoelectric elements along said array direction, and wherein said conductive member is fixed to said conductive material layer by said filled conductive material.

18. The ultrasound transducer array according to claim 17, wherein said conductive member is a conductive material formed into any of those among a wire shape, ribbon shape, rod shape, or foil shape.

19. The ultrasound transducer array according to claim 17, wherein the ratio of the width w in the array direction to the thickness t in the ultrasound radiation direction of said plurality of piezoelectric elements is from 0.3 to 0.5.

20. The ultrasound transducer array according to claim 19, wherein the ratio of the width w in the array direction to the thickness t in the ultrasound radiation direction of said plurality of piezoelectric elements is from 0.4 to 0.5.

21. The ultrasound transducer array according to claim 1, wherein the ratio of the width w in the array direction to the thickness t in the ultrasound radiation direction of said plurality of piezoelectric elements is from 0.3 to 0.5.

22. The ultrasound transducer array according to claim 21, wherein the ratio of the width w in the array direction to the thickness t in the ultrasound radiation direction of said plurality of piezoelectric elements is from 0.4 to 0.5.

* * * * *